United States Patent
Zhang et al.

(10) Patent No.: US 10,416,087 B2
(45) Date of Patent: Sep. 17, 2019

(54) SYSTEMS AND METHODS FOR DEFECT DETECTION USING IMAGE RECONSTRUCTION

(71) Applicant: KLA-Tencor Corporation, Milpitas, CA (US)

(72) Inventors: Jing Zhang, Milpitas, CA (US); Jeremy Nesbitt, San Jose, CA (US); Grace Hsiu-Ling Chen, Los Gatos, CA (US); Richard Wallingford, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 181 days.

(21) Appl. No.: 15/357,888

(22) Filed: Nov. 21, 2016

(65) Prior Publication Data

US 2017/0191945 A1 Jul. 6, 2017

Related U.S. Application Data

(60) Provisional application No. 62/274,169, filed on Jan. 1, 2016.

(51) Int. Cl.
*G06K 9/20* (2006.01)
*G06K 9/36* (2006.01)
(Continued)

(52) U.S. Cl.
CPC ..... *G01N 21/8851* (2013.01); *G01N 21/9501* (2013.01); *G06T 3/4053* (2013.01);
(Continued)

(58) Field of Classification Search
CPC ...... G01N 21/9501–9505; G01N 2021/95676; G01N 21/956; G01N 21/95607;
(Continued)

(56) References Cited

U.S. PATENT DOCUMENTS

| 6,154,714 A | 11/2000 | Lepejian |
| 6,529,621 B1 | 3/2003 | Glasser et al. |

(Continued)

FOREIGN PATENT DOCUMENTS

| JP | 2005037166 A | * | 2/2005 | ........... G01N 21/956 |
| JP | 2015133069 A | * | 7/2015 | ............... G06T 5/20 |

OTHER PUBLICATIONS

Fish et al., "Blind deconvolution by means of the Richardson-Lucy algorithm", J. Opt. Soc. Am. A/vol. 12, No. 1/Jan. 1995, pp. 58-65 plus 9 additional pages of photographs. (Year: 1995).*

(Continued)

*Primary Examiner* — Brian Werner
(74) *Attorney, Agent, or Firm* — Suiter Swantz pc llo

(57) ABSTRACT

An inspection system includes an illumination sub-system, a collection sub-system, and a controller. The illumination sub-system includes an illumination source configured to generate a beam of illumination and a set of illumination optics to direct the beam of illumination to a sample. The collection sub-system includes a set of collection optics to collect illumination emanating from the sample and a detector configured to receive the collected illumination from the sample. The controller is configured to acquire a test image of the sample, reconstruct the test image to enhance the resolution of the test image, and detect one or more defects on the sample based on the reconstructed test image.

35 Claims, 22 Drawing Sheets

(51) Int. Cl.
*G06K 9/62* (2006.01)
*G01N 21/88* (2006.01)
*G01N 21/95* (2006.01)
*G06T 3/40* (2006.01)
*G06T 5/00* (2006.01)
*G06T 7/00* (2017.01)

(52) U.S. Cl.
CPC .............. *G06T 5/003* (2013.01); *G06T 7/001* (2013.01); *G06T 7/0006* (2013.01); *G01N 2021/8887* (2013.01); *G06T 2207/10004* (2013.01); *G06T 2207/10056* (2013.01); *G06T 2207/20056* (2013.01); *G06T 2207/20076* (2013.01); *G06T 2207/20081* (2013.01); *G06T 2207/30148* (2013.01)

(58) Field of Classification Search
CPC ............ G01N 21/9503; G01N 23/2251; G06T 2207/30148; G06T 7/0004; G06T 5/003
See application file for complete search history.

(56) References Cited

U.S. PATENT DOCUMENTS

| | | |
|---|---|---|
| 6,691,052 B1 | 2/2004 | Maurer |
| 6,748,103 B2 | 6/2004 | Glasser et al. |
| 6,920,596 B2 | 7/2005 | Sagatelian et al. |
| 6,921,672 B2 | 7/2005 | Satya et al. |
| 6,930,309 B1 | 8/2005 | Mankos et al. |
| 6,948,141 B1 | 9/2005 | Satya et al. |
| 6,966,047 B1 | 11/2005 | Glasser |
| 6,995,393 B2 | 2/2006 | Weiner et al. |
| 7,570,796 B2 | 8/2009 | Zafar et al. |
| 7,676,077 B2 | 3/2010 | Kulkarni et al. |
| 8,041,103 B2 | 10/2011 | Kulkarni et al. |
| 8,112,241 B2 | 2/2012 | Xiong |
| 8,126,255 B2 | 2/2012 | Bhaskar et al. |
| 8,194,968 B2 | 6/2012 | Park et al. |
| 8,611,639 B2 | 12/2013 | Kulkarni et al. |
| 8,702,566 B2 | 4/2014 | Mazzanobile et al. |
| 8,947,521 B1* | 2/2015 | Hill ................... G01N 21/9501 348/295 |
| 9,222,895 B2 | 12/2015 | Duffy et al. |
| 2006/0069460 A1 | 3/2006 | Smith et al. |
| 2008/0279444 A1 | 11/2008 | Fischer et al. |
| 2013/0114085 A1 | 5/2013 | Wang et al. |
| 2014/0212021 A1 | 7/2014 | Amzaleg et al. |
| 2015/0029324 A1* | 1/2015 | Tanabe ............... G01N 21/8851 348/79 |
| 2016/0078600 A1* | 3/2016 | Perez Pellitero ..... G06T 3/4053 382/155 |

OTHER PUBLICATIONS

Zhang et al., "Bregmanized Nonlocal Regularization for Deconvolution and Sparse Reconstruction", SIAM Journal on Imaging Sciences, 2010, vol. 3, No. 3; 4 bib pages, and pp. 1-25. (Year: 2010).*

Starck, J.L., et al, "Deconvolution in Astronomy: A Review," Publications of the Astronomical Society of the Pacific, 114:1051-1069 (2002).

Wang, R, et al, "Recent Progress in Image Debluring," arXiv:1409.6838 [cs.CV] (2014).

Richardson, WH, "Bayesian-based iterative method of image restoration," ournal of the Optical Society of America 62(1):55-59 (1972).

Lucy, LB, "An iterative technique for the rectification of observed distributions," The astronomical journal 79:745-754 (1974).

Dey, N. et al, "3D Microscopy Deconvolution using Richardsion-Lucy Algorithm with Total Variation Regularization," Institut National de Recherche en Informatique et en Automatique, N. 5272 (2004).

Yuan, L., et al, "Progressive Inter-scale and Intra-scale Non-blind Image Deconvolution," ACM Transactions on Graphics (TOG)—Proceedings of ACM SIGGRAPH 2008, 24(3), Art. 74 (2008).

* cited by examiner

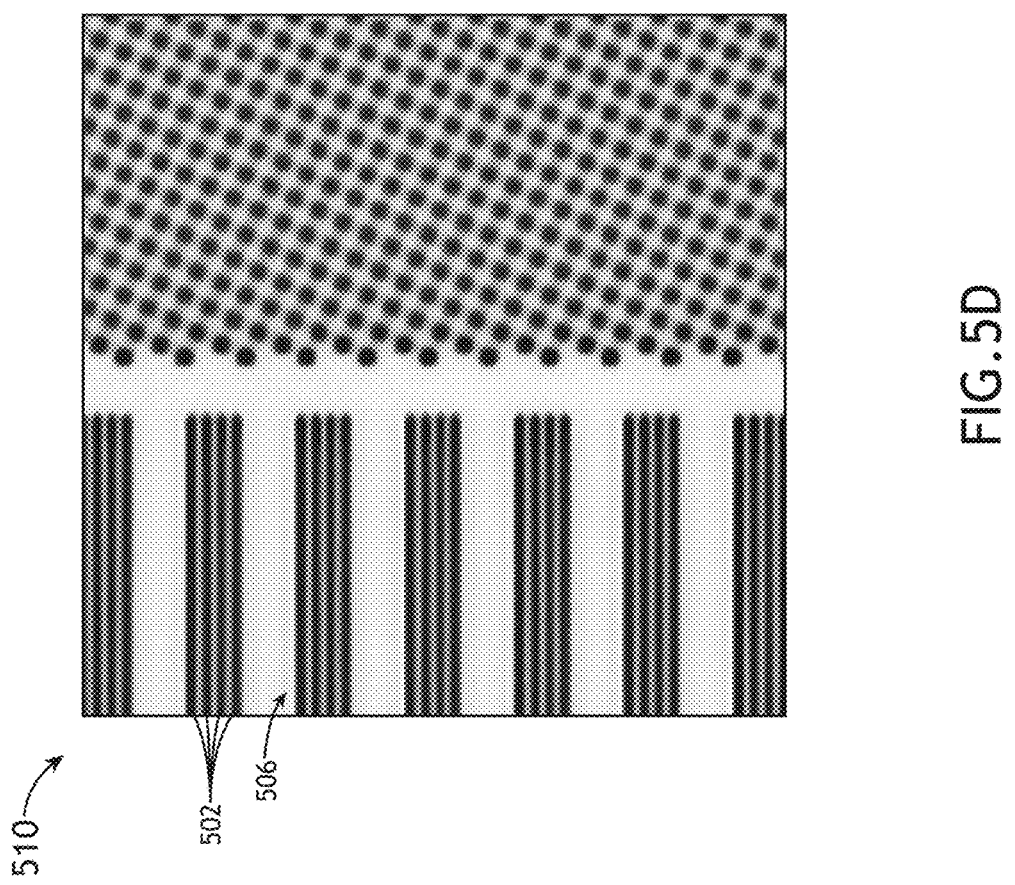

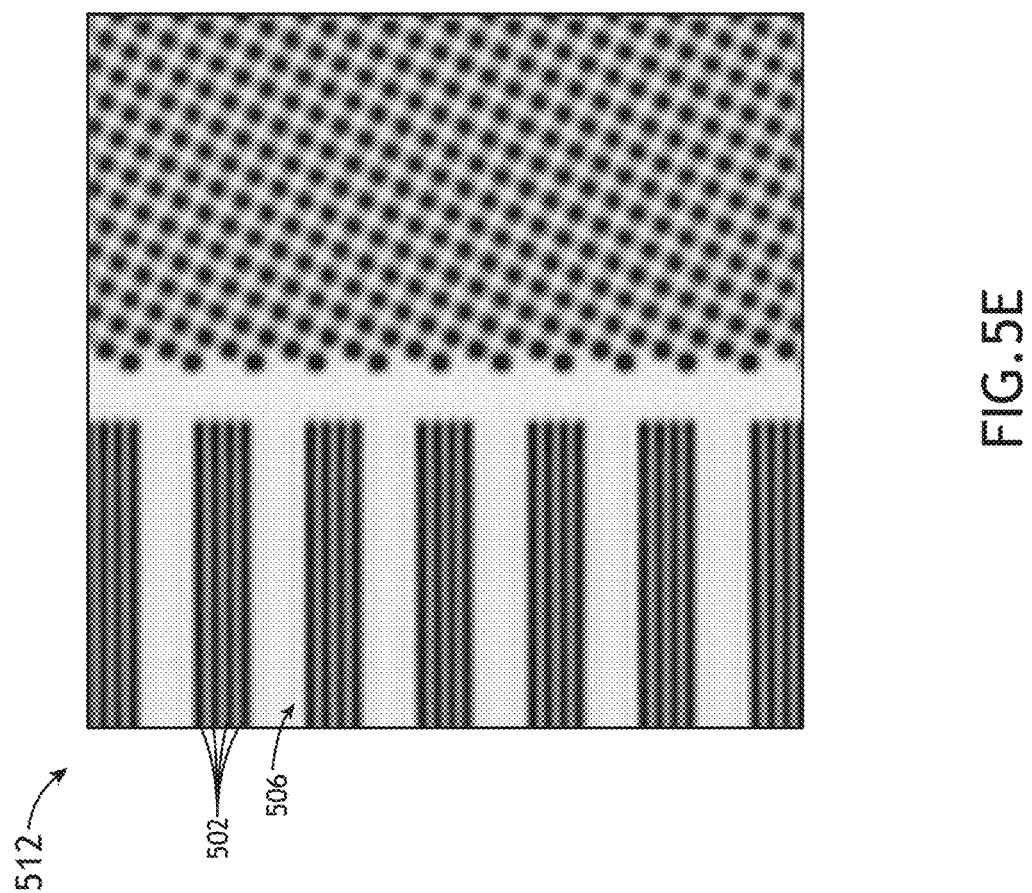

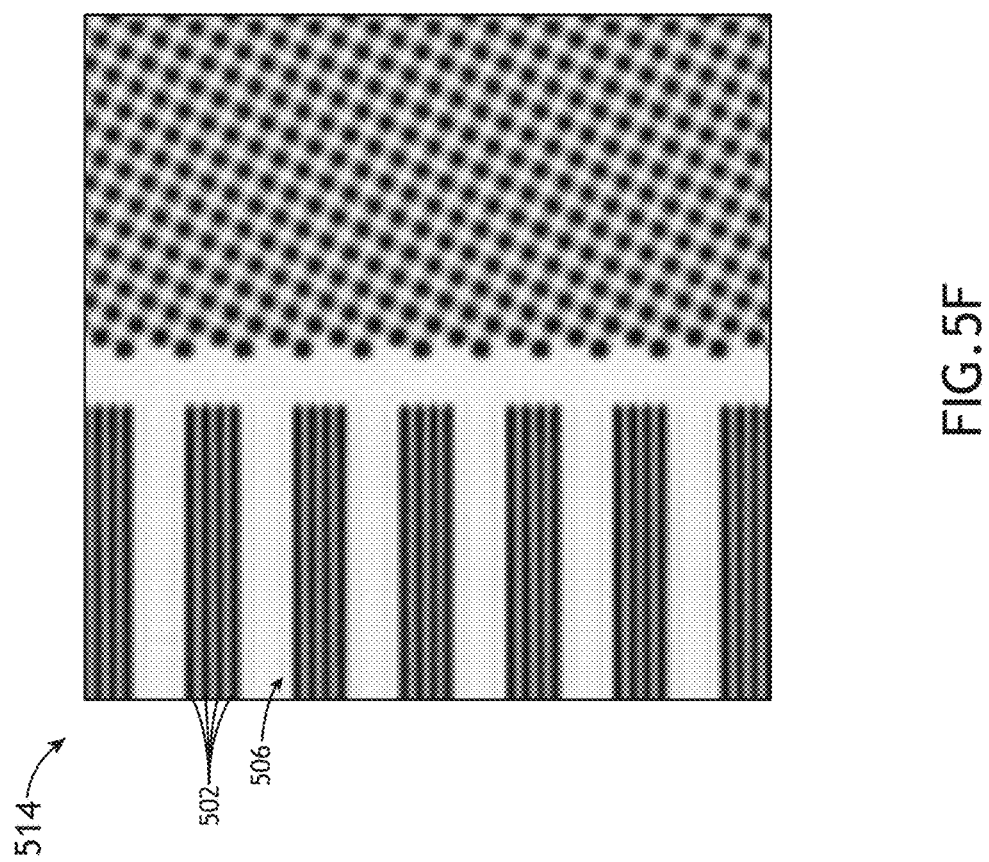

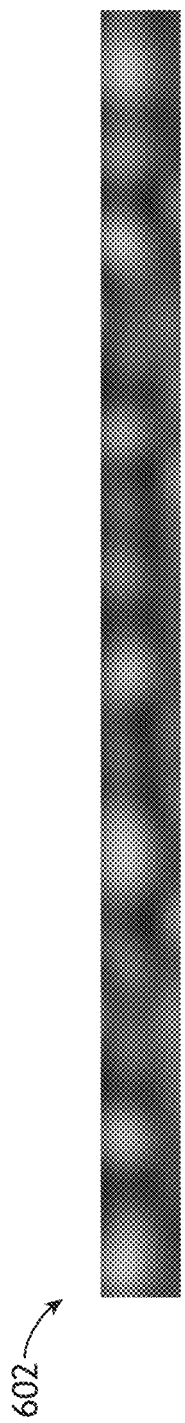
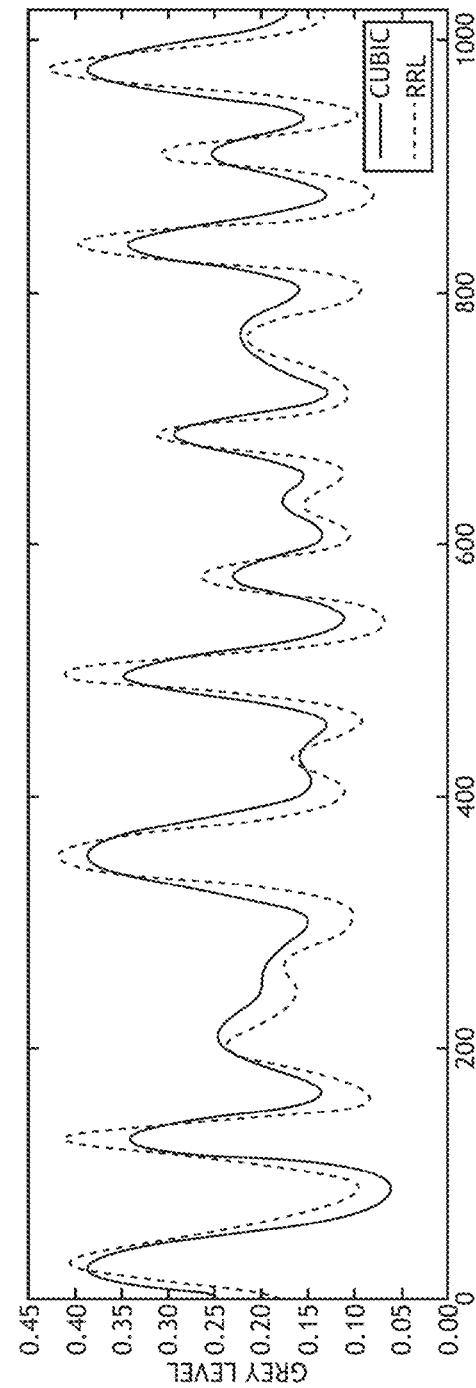
FIG. 6A
FIG. 6B
FIG. 6C

SYSTEMS AND METHODS FOR DEFECT DETECTION USING IMAGE RECONSTRUCTION

CROSS-REFERENCE TO RELATED APPLICATION

The present application claims the benefit under 35 U.S.C. § 119(e) of U.S. Provisional Application Ser. No. 62/274,169, filed Jan. 1, 2016, entitled APPLICATION OF SUPER-RESOLUTION TO IMPROVE WAFER INSPECTION, naming Jing Zhang, Jeremy Nesbitt, Grace Chen, and Dick Wallingford as inventors, which is incorporated herein by reference in the entirety.

TECHNICAL FIELD

The present disclosure relates generally to defect detection, and, more particularly, to detecting defects based on reconstructed images.

BACKGROUND

Inspection systems identify and classify defects on semiconductor wafers to generate a defect population on a wafer. A given semiconductor wafer may include hundreds of chips, each chip containing thousands of components of interest, and each component of interest may have millions of instances on a given layer of a chip. As a result, inspection systems may generate vast numbers of data points (e.g. hundreds of billions of data points for some systems) on a given wafer. Further, the demand for ever-shrinking devices leads to increased demands on inspection systems. The demands include the need for increased resolution and capacity without sacrificing inspection speed or sensitivity.

Additionally, many semiconductor devices have dimensions smaller than the resolution of an inspection system, which causes images generated by the inspection system to appear blurry. In extreme cases, images generated by the inspection system may not closely resemble the actual pattern of features on the wafer. As a result, the signal to noise ratio of defect signals may suffer and may negatively impact performance. Therefore, it would be desirable to provide a system and method for curing shortcomings such as those identified above.

SUMMARY

An inspection system is disclosed, in accordance with one or more illustrative embodiments of the present disclosure. In one illustrative embodiment, the system includes an illumination sub-system. In another illustrative embodiment, the illumination sub-system includes an illumination source configured to generate a beam of illumination. In another illustrative embodiment, the illumination sub-system includes a set of illumination optics to direct the beam of illumination to a sample. In another illustrative embodiment, the system includes a collection sub-system. In another illustrative embodiment, the collection sub-system includes a set of collection optics to collect illumination emanating from the sample. In another illustrative embodiment, the collection sub-system includes a detector configured to receive the collected illumination from the sample. In another illustrative embodiment, the system includes a controller communicatively coupled to the detector. In another illustrative embodiment, the controller includes a memory device and one or more processors. In another illustrative embodiment, the controller is configured to acquire a test image of the sample. In another illustrative embodiment, the controller is configured to reconstruct the test image to enhance the resolution of the test image. In another illustrative embodiment, the controller is configured to detect one or more defects on the sample based on the reconstructed test image.

An inspection system is disclosed, in accordance with one or more illustrative embodiments of the present disclosure. In one illustrative embodiment, the system includes an illumination sub-system. In another illustrative embodiment, the illumination sub-system includes an illumination source configured to generate a beam of illumination. In another illustrative embodiment, the illumination sub-system includes a set of illumination optics to direct the beam of illumination to a sample. In another illustrative embodiment, the system includes a collection sub-system. In another illustrative embodiment, the collection sub-system includes a set of collection optics to collect illumination emanating from the sample. In another illustrative embodiment, the collection sub-system includes a detector configured to receive the collected illumination from the sample. In another illustrative embodiment, the system includes a controller communicatively coupled to the detector. In another illustrative embodiment, the controller includes a memory device and one or more processors. In another illustrative embodiment, the controller is configured to acquire a test image of the sample. In another illustrative embodiment, the controller is configured to detect one or more defects on the sample based on the test image. In another illustrative embodiment, the controller is configured to generate one or more patch images associated with the one or more detected defects on the sample. In another illustrative embodiment, the controller is configured to reconstruct the one or more patch images to enhance the resolution of the one or more patch images. In another illustrative embodiment, the controller is configured to classify the one or more defects based on the one or more reconstructed patch images.

A multi-mode inspection system is disclosed, in accordance with one or more illustrative embodiments of the present disclosure. In one illustrative embodiment, the system includes an illumination sub-system. In another illustrative embodiment, the illumination sub-system includes an illumination source configured to generate two or more modes of illumination. In another illustrative embodiment, the illumination sub-system includes a set of illumination optics to direct the beam of illumination to a sample. In another illustrative embodiment, the system includes a collection sub-system. In another illustrative embodiment, the collection sub-system includes a set of collection optics to collect illumination emanating from the sample. In another illustrative embodiment, the collection sub-system includes an adjustable collection aperture to generate two or more collection modes. In another embodiment, the illumination sub-system includes two or more system modes formed from the two or more modes of illumination and the two or more collection modes. In another illustrative embodiment, the collection sub-system includes a detector configured to receive the collected illumination from the sample. In another illustrative embodiment, the system includes a controller communicatively coupled to the detector. In another illustrative embodiment, the controller includes a memory device and one or more processors. In another illustrative embodiment, the controller is configured to acquire two or more test images of the sample based on the two or more system modes. In another illustrative embodiment, the controller is configured to estimate a point spread function of the inspection system. In another illustrative embodiment, the controller is configured to reconstruct the two or more test images to enhance the resolution of the two or more test images based on the estimated point spread function. In another illustrative embodiment, the controller is configured to identify one or more defects on the sample based on the two or more reconstructed test images.

An inspection system is disclosed, in accordance with one or more illustrative embodiments of the present disclosure. In one illustrative embodiment, the system includes an illumination sub-system. In another illustrative embodiment, the illumination sub-system includes an illumination source configured to generate a beam of illumination. In another illustrative embodiment, the illumination sub-system includes a set of illumination optics to direct the beam of illumination to a sample. In another illustrative embodiment, the system includes a collection sub-system. In another illustrative embodiment, the collection sub-system includes a set of collection optics to collect illumination emanating from the sample. In another illustrative embodiment, the collection sub-system includes a detector configured to receive the collected illumination from the sample. In another illustrative embodiment, the system includes a controller communicatively coupled to the detector. In another illustrative embodiment, the controller includes a memory device and one or more processors. In another illustrative embodiment, the controller is configured to configure a defect detection recipe. In another illustrative embodiment, the controller is configured to detect one or more defects on the sample based on the defect detection recipe.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF DRAWINGS

The numerous advantages of the disclosure may be better understood by those skilled in the art by reference to the accompanying figures in which:

FIG. 5D is a reconstructed image generated using regularized Richardson-Lucy deconvolution with a Total Variation regularization factor, in accordance with one or more embodiments of the present disclosure.

FIG. 5E is a reconstructed image generated using regularized Richardson-Lucy deconvolution with a Tikhonov-Miller regularization factor, in accordance with one or more embodiments of the present disclosure.

FIG. 5F is a reconstructed image generated using regularized Richardson-Lucy deconvolution with a bilateral regularization factor, in accordance with one or more embodiments of the present disclosure.

FIG. 6A is an image of a sample reconstructed using cubic interpolation, in accordance with one or more embodiments of the present disclosure.

FIG. 6B is an image of the same portion of the sample reconstructed using regularized Richardson-Lucy deconvolution, in accordance with one or more embodiments of the present disclosure.

FIG. 6C is a plot illustrating the gray level associated with a slice of both FIG. 6A and FIG. 6B, in accordance with one or more embodiments of the present disclosure.

DETAILED DESCRIPTION

Figure 1A:
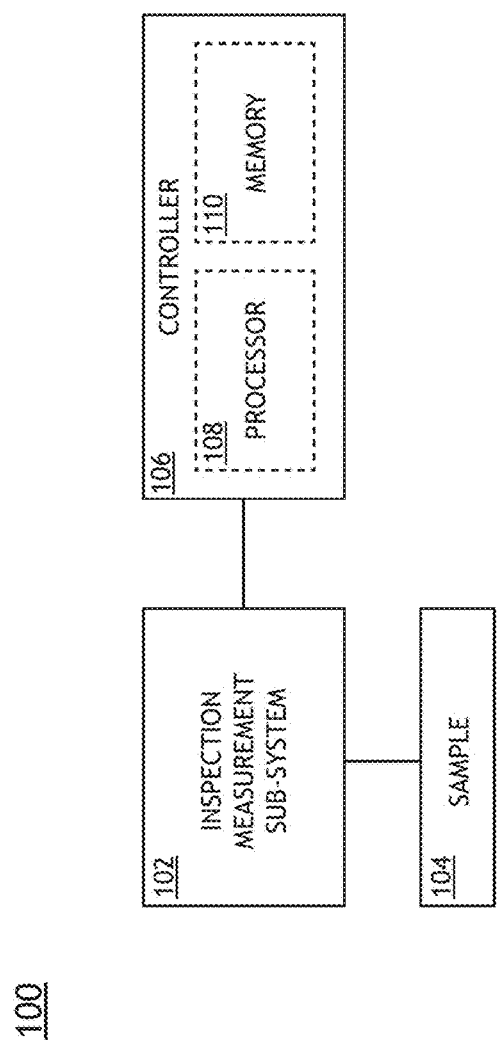
FIG. 1A is a conceptual view of an inspection system, in accordance with one or more embodiments of the present disclosure.

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Referring generally to FIGS. 1A through 14, systems and methods for inspecting a sample for defects using super-resolution image reconstruction are disclosed. Embodiments of the present disclosure are directed to reconstructing one or more images to facilitate defect detection. Image reconstruction may provide, but is not limited to providing, enhanced resolution or an enhanced signal to noise ratio (SNR) of defects. Embodiments of the present disclosure are directed to reconstructing a single image (e.g. a test image of the sample). Additional embodiments of the present disclosure are directed to reconstructing multiple images for defect detection. For example, a test image of the sample as well as a reference image of the sample may be separately reconstructed. Further, a difference image based on the reconstructed test image and the reconstructed reference image may be generated for defect detection.

It is recognized herein that feature sizes on semiconductor wafers may be significantly smaller than the resolution of optical inspection systems utilized to detect defects on the wafers. Put another way, the size of fabricated features as well as any potential defects may be significantly smaller than a detection wavelength of an optical inspection system. Accordingly, an optical inspection system of a wafer may not fully resolve many sample features such that an image generated by the inspection system may appear blurry. For example, an image generated by an optical inspection system may lack much of the high spatial frequency content of the design pattern on the sample. Further, the interaction of an illumination beam of the inspection system and features on the sample may result in scattering and optical interference effects that may further affect the image.

It is further recognized herein that image reconstruction techniques such as, but not limited to, image interpolation or deconvolution, may be utilized to enhance a blurry image. For example, image interpolation may be utilized to up-scale an image to increase the resolution of an image. By way of another example, deconvolution (e.g. image deblur) may be used to restore shape content to an image by reversing known or estimated distortions induced by the imaging system. Distortions of the imaging system may be described by a point spread function (PSF), which describes the response of an optical system to a point source (e.g. the impulse response of an inspection system). An image provided by an inspection system may thus be characterized as a convolution of the actual image field (e.g. a patterned semiconductor wafer) and the PSF. Accordingly, image deconvolution may reverse the optical distortions induced by deconvolving the image with the PSF to produce an enhanced reconstructed image. Further, deconvolution techniques may be classified based on the knowledge of the PSF. Non-blind deconvolution techniques utilize a known (or estimated) PSF based on prior knowledge of the imaging system, whereas blind deconvolution techniques estimate the PSF based on analysis of the image itself.

In general, precisely determining the PSF of an imaging system is not practical. For example, the PSF may vary based on the position of a point source in the image field and/or the depth of a point source (e.g. the degree of defocus). Additionally, motion of an object or jitter of the system may further impact the PSF associated with a particular image. Accordingly, non-blind deconvolution techniques generally utilize an estimated PSF.

In the context of defect detection on a sample having features smaller than the resolution of the inspection system, the true PSF may be a function of the local design of the sample such that a global PSF may not be defined that would apply to images of any arbitrary design pattern. However, a complete reconstruction of the actual features on a sample may not be required to detect defects on the sample. Embodiments of the present disclosure utilize an estimated global PSF to enhance the resolution of an image of the sample for defect detection. In this regard, a reconstructed image may provide an enhanced signal to noise ratio (SNR) of defects.

Additional embodiments of the present disclosure are directed to image reconstruction using regularized deconvolution. In this regard, image reconstruction may utilize iterative deconvolution steps including one or more regularization terms as constraints based on prior knowledge of known or expected results to converge to a likely solution. Accordingly, regularization terms in a cost function associated with deconvolution may avoid unlikely solutions and/or avoid image artifacts such as, but not limited to, ringing artifacts. Embodiments of the present disclosure utilize sparse distribution regularization terms to reconstruct images having sparsely distributed defects. Further embodiments of the present disclosure utilize image-constraining regularization terms to reconstruct images based on prior knowledge of one or more aspects of an image of the sample. For example, image-constraining regularization terms may include, but are not limited to, image-gradient regularization terms (e.g. Total Variation, Tikhonov-Miller, Bilaterial, or the like).

Deconvolution techniques are generally described in Starck, J. L., et al, "Deconvolution in Astronomy: A Review," Publications of the Astronomical Society of the Pacific, 114:1051-1069 (2002), which is incorporated herein by reference in its entirety. Image deblurring is described generally in Wang, R, et al, "Recent Progress in Image Deblurring," arXiv:1409.6838 [cs.CV] (2014), which is incorporated herein by reference in its entirety. Bayesian-based iterative methods for image restoration are described generally in Richardson, W H, "Bayesian-based iterative method of image restoration," Journal of the Optical Society of America 62(1):55-59 (1972), which is incorporated herein by reference in its entirety. An iterative rectification technique is described generally in Lucy, L B, "An iterative technique for the rectification of observed distributions," The astronomical journal 79:745-754 (1974), which is incorporated herein by reference in its entirety. Three-dimensional deconvolution techniques using Richardson-Lucy algorithms with Total Variation regularization is described generally in Dey, N. et al, "3D Microscopy Deconvolution using Richardson-Lucy Algorithm with Total Variation Regularization," Institut National de Recherche en Informatique et en Automatique, N. 5272 (2004), which is incorporated herein by reference in its entirety. Progressive inter-scale and intra-scale non-blind image deconvolution is generally described in Yuan, L., et al, "Progressive Inter-scale and Intra-scale Non-blind Image Deconvolution," ACM Transactions on Graphics (TOG)—Proceedings of ACM SIGGRAPH 2008, 24(3), Art. 74 (2008), which is incorporated herein by reference in its entirety.

It is recognized herein that typical defect detection systems may detect defects by comparing a test image to one or more reference images (e.g. by the generation of one or more difference images, or the like). A reference image may be associated with another die (e.g. die-to-die detection, or the like) or another cell (e.g. cell-to-cell detection, or the like). For example, defects in a sample die may be characterized by comparing an image of the sample die with an image of a reference die (e.g. die-to-die (D2D) inspection, standard reference die (SRD) inspection, or the like) or by comparing an image of the sample die with an image based on design characteristics (e.g. die-to-database (D2DB) inspection). Inspection systems using persistent data (e.g. stored data) is generally described in U.S. Pat. No. 8,126,255, issued on Feb. 28, 2012, which is incorporated herein by reference in its entirety. Inspection systems using design data of a sample to facilitate inspection is generally described in U.S. Pat. No. 7,676,077, issued on Mar. 9, 2010, and U.S. Pat. No. 6,154,714, issued on Nov. 28, 2000, which are incorporated herein by reference in their entirety. Embodiments of the present disclosure are directed to reconstructing a test image and a reference image prior to generating a difference image. For example, both the test image and the reference image may be reconstructed through deconvolution with an estimated PSF of the inspection system. The test image and/or the reference image may be deconvolved using an image constraining regularization term (e.g. an image gradient constraining regularization term, or the like) to avoid unlikely solutions and to avoid artifacts. Additionally, a sparse distribution regularization term may be further incorporated into the deconvolution of the test image. In this regard, the differences between the test image and the reference image (e.g. the defect signals to be detected) may be emphasized.

Additional embodiments of the present disclosure are directed to reconstructing multiple test images. For example, test images of a sample taken with multiple illumination modes (e.g. multiple illumination angles, or the like) may be separately reconstructed and analyzed for defects. Further, the multiple reconstructed test images may be combined to form a combined image suitable for defect detection. By way of another example, patch images associated with localized areas around detected defects on a sample may be reconstructed. For example, an inspection system may generate one or more patch images, each having an expected defect and a portion of the image surrounding the defect, for defect classification. In this regard, reconstruction of the patch images may provide enhanced defect classification or location-determination of a defect with respect to designed sample patterns (e.g. unresolved in the patch image).

Additional embodiments of the present disclosure are directed to reconstructing anti-aliased test images. For example, an inspection system may utilize large pixel sizes (e.g. with respect to sample features) to improve throughput or to optimally utilize the light level associated with an illumination source. However, such images may suffer from aliasing noise. Accordingly, the inspection system may utilize an anti-aliasing technique (e.g. application of an anti-aliasing filter, intentional blurring during image acquisition, or the like). Embodiments of the present disclosure are directed to reconstructing anti-aliased images to recover portions of a defect signal impacted by anti-aliasing.

Additional embodiments of the present disclosure are directed to reconstructing configuration images generated by the inspection system for determining run-time image acquisition parameters for defect detection on a particular sample (e.g. a recipe). For example, a configuration image of a sample generated by the inspection system may be reconstructed to facilitate the determination of parameters associated with radiometric systems (e.g. a light level during test image acquisition based on the dynamic range of the configuration image, or the like), the determination of one or more care areas on the sample to interrogate, or to train design-based inspection algorithms (e.g. pixel-to-design alignment (PDA), context-based imaging (CBI), template-based imaging (TBI), or the like).

As used throughout the present disclosure, the term "sample" generally refers to a substrate formed of a semiconductor or non-semiconductor material (e.g. a wafer, or the like). For example, a semiconductor or non-semiconductor material may include, but is not limited to, monocrystalline silicon, gallium arsenide, and indium phosphide. A sample may include one or more layers. For example, such layers may include, but are not limited to, a resist, a dielectric material, a conductive material, and a semiconductive material. Many different types of such layers are known in the art, and the term sample as used herein is intended to encompass a sample on which all types of such layers may be formed. One or more layers formed on a sample may be patterned or unpatterned. For example, a sample may include a plurality of dies, each having repeatable patterned features. Formation and processing of such layers of material may ultimately result in completed devices. Many different types of devices may be formed on a sample, and the term sample as used herein is intended to encompass a sample on which any type of device known in the art is being fabricated. Further, for the purposes of the present disclosure, the term sample and wafer should be interpreted as interchangeable. In addition, for the purposes of the present disclosure, the terms patterning device, mask and reticle should be interpreted as interchangeable.

FIG. 1A is a conceptual view illustrating an inspection system 100, in accordance with one or more embodiments of the present disclosure. In one embodiment, the inspection system 100 includes an inspection measurement sub-system 102 to interrogate a sample 104. For example, the inspection measurement sub-system 102 may detect one or more defects on the sample 104.

It is noted herein that inspection measurement sub-system 102 may be any type of inspection system known in the art suitable for detecting defects on a sample 104. For example, the inspection measurement sub-system 102 may include a particle-beam inspection sub-system. Accordingly, inspection measurement sub-system 102 may direct one or more particle beams (e.g. electron beams, ion beams, or the like) to the sample 104 such that one or more defects are detectable based on detected radiation emanating from the sample 104 (e.g. secondary electrons, backscattered electrons, luminescence, or the like). As another example, inspection measurement sub-system 102 may include an optical inspection sub-system. Accordingly, inspection measurement sub-system 102 may direct optical radiation to the sample 104 such that one or more defects are detectable based on detected radiation emanating from the sample 104 (e.g. reflected radiation, scattered radiation, diffracted radiation, luminescent radiation, or the like).

The inspection measurement sub-system 102 may operate in an imaging mode or a non-imaging mode. For example, in an imaging mode, individual objects (e.g. defects) may be resolvable within the illuminated spot on the sample (e.g. as part of a bright-field image, a dark-field image, a phase-contrast image, or the like). In a non-imaging mode of operation, radiation collected by one or more detectors may be associated with a single illuminated spot on the sample and may represent a single pixel of an image of the sample 104. In this regard, an image of the sample 104 may be generated by acquiring data from an array of sample locations. Further, the inspection measurement sub-system 102 may operate as a scatterometry-based inspection system in which radiation from the sample is analyzed at a pupil plane to characterize the angular distribution of radiation from the sample 104 (e.g. associated with scattering and/or diffraction of radiation by the sample 104).

In another embodiment, the inspection system 100 includes a controller 106 coupled to the inspection measurement sub-system 102. In this regard, the controller 106 may be configured to receive data including, but not limited to, inspection data from the inspection measurement sub-system 102. In another embodiment, the controller 106 includes one or more processors 108. For example, the one or more processors 108 may be configured to execute a set of program instructions maintained in a memory device 110, or memory. The one or more processors 108 of a controller 106 may include any processing element known in the art. In this sense, the one or more processors 108 may include any microprocessor-type device configured to execute algorithms and/or instructions. Further, the memory device 110 may include any storage medium known in the art suitable for storing program instructions executable by the associated one or more processors 108. For example, the memory device 110 may include a non-transitory memory medium. As an additional example, the memory device 110 may include, but is not limited to, a read-only memory, a random access memory, a magnetic or optical memory device (e.g., disk), a magnetic tape, a solid state drive and the like. It is further noted that memory device 110 may be housed in a common controller housing with the one or more processors 108.

Figure 1B:
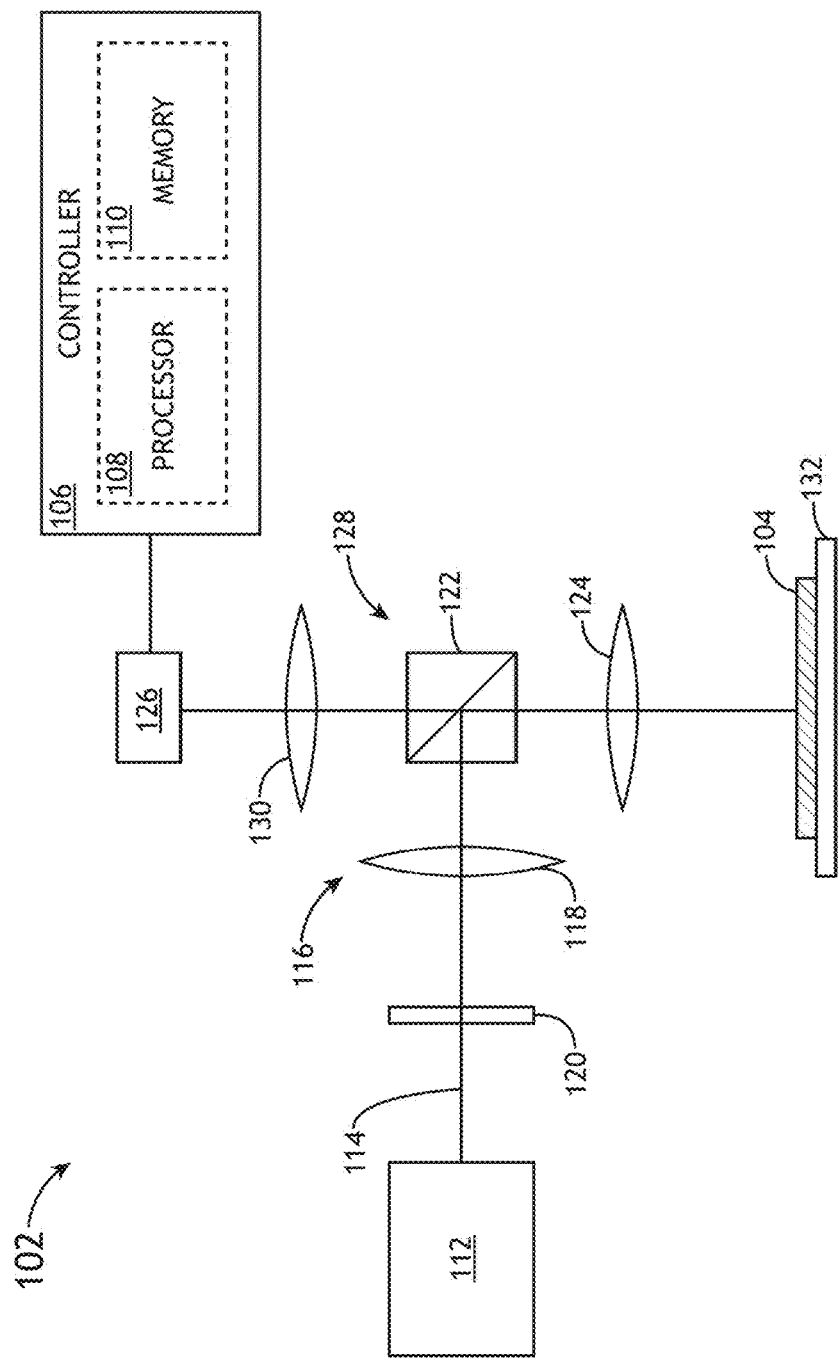
FIG. 1B is a conceptual view of the inspection measurement sub-system, in accordance with one or more embodiments of the present disclosure.

FIG. 1B is a conceptual view illustrating the inspection measurement sub-system 102, in accordance with one or more embodiments of the present disclosure. In one embodiment, the inspection measurement sub-system 102 includes an illumination source 112 to generate an illumination beam 114. In a further embodiment, the illumination source 112 is a separate illumination source configured to generate a separate illumination beam 114. The illumination beam 114 may include one or more selected wavelengths of light including, but not limited to, ultraviolet (UV) radiation, visible radiation, or infrared (IR) radiation.

In another embodiment, the illumination source 112 directs the illumination beam 114 to the sample 104 via an illumination pathway 116. The illumination pathway 116 may include one or more lenses 118. Further, the illumination pathway 116 may include one or more additional optical components 120 suitable for modifying and/or conditioning the illumination beam 114. For example, the one or more optical components 120 may include, but are not limited to, one or more polarizers, one or more filters, one or more beam splitters, one or more diffusers, one or more homogenizers, one or more apodizers, or one or more beam shapers. In one embodiment, the illumination pathway 116 includes a beamsplitter 122. In another embodiment, the inspection measurement sub-system 102 includes an objective lens 124 to focus the illumination beam 114 onto the sample 104.

In another embodiment, the inspection measurement sub-system 102 includes one or more detectors 126 configured to capture radiation emanating from the sample 104 through a collection pathway 128. The collection pathway 128 may include multiple optical elements to direct and/or modify illumination collected by the objective lens 124 including, but not limited to one or more lenses 130, one or more filters, one or more polarizers, one or more beam blocks, or one or more beamsplitters.

For example, a detector 126 may receive an image of the sample 104 provided by elements in the collection pathway 128 (e.g. the objective lens 124, the one or more lenses 130, or the like). By way of another example, a detector 126 may receive radiation reflected or scattered (e.g. via specular reflection, diffuse reflection, and the like) from the sample 104. By way of another example, a detector 126 may receive radiation generated by the sample (e.g. luminescence associated with absorption of the illumination beam 114, and the like). By way of another example, a detector 126 may receive one or more diffracted orders of radiation from the sample 104 (e.g. 0-order diffraction, ±1 order diffraction, ±2 order diffraction, and the like). Further, it is noted herein that the one or more detectors 126 may include any optical detector known in the art suitable for measuring illumination received from the sample 104. For example, a detector 126 may include, but is not limited to, a CCD detector, a TDI detector, a photomultiplier tube (PMT), an avalanche photodiode (APD), or the like. In another embodiment, a detector 126 may include a spectroscopic detector suitable for identifying wavelengths of radiation emanating from the sample 104. Further, the inspection measurement sub-system 102 may include multiple detectors 126 (e.g. associated with multiple beam paths generated by one or more beamsplitters to facilitate multiple metrology measurements (e.g. multiple metrology tools) by the inspection measurement sub-system 102).

In another embodiment, the inspection measurement sub-system 102 is communicatively coupled to the controller 106 of inspection system 100. In this regard, the controller 106 may be configured to receive data including, but not limited to, inspection data (e.g. inspection measurement results, images of the target, pupil images, and the like) or metrology metrics (e.g. precision, tool-induced shift, sensitivity, diffraction efficiency, through-focus slope, side wall angle, critical dimensions, and the like).

In another embodiment, the sample 104 is disposed on a sample stage 132 suitable for securing the sample 104 during scanning. In another embodiment, the sample stage 132 is an actuatable stage. For example, the sample stage 132 may include, but is not limited to, one or more translational stages suitable for selectably translating the sample 104 along one or more linear directions (e.g., x-direction, y-direction and/or z-direction). By way of another example, the sample stage 132 may include, but is not limited to, one or more rotational stages suitable for selectably rotating the sample 104 along a rotational direction. By way of another example, the sample stage 132 may include, but is not limited to, a rotational stage and a translational stage suitable for selectably translating the sample along a linear direction and/or rotating the sample 104 along a rotational direction.

Figure 1C:
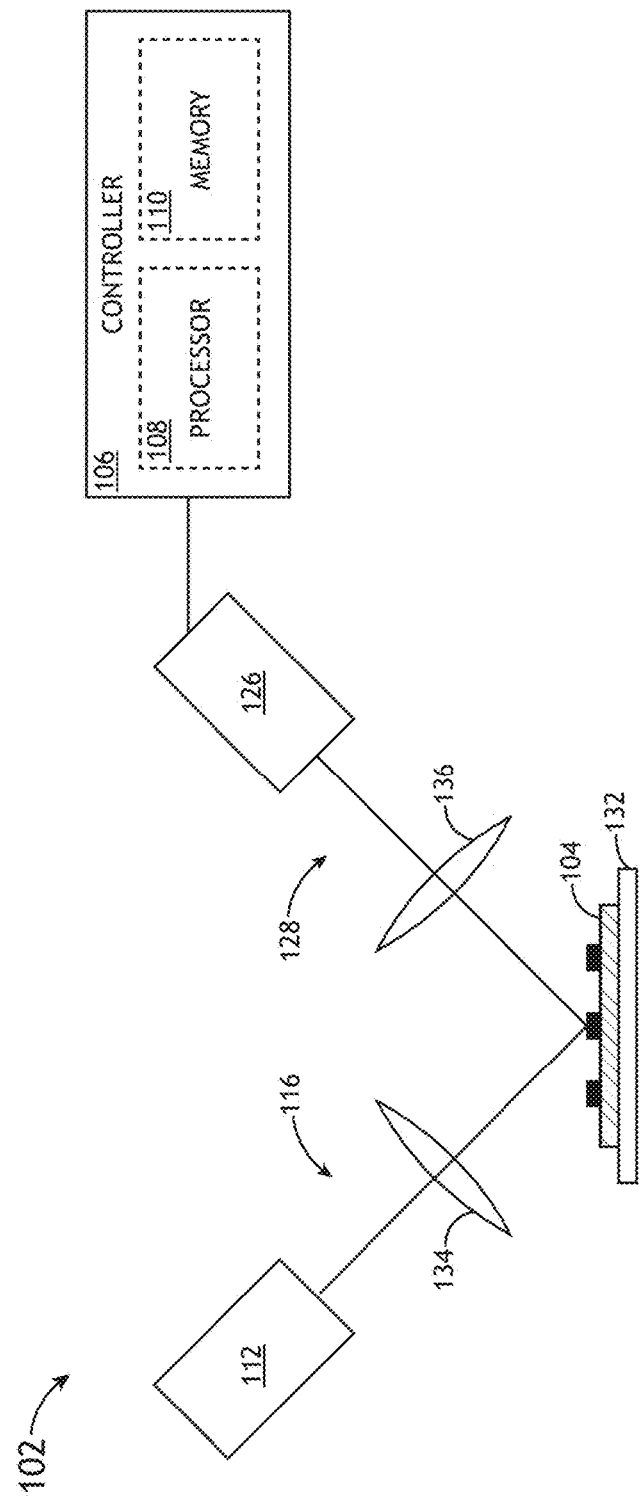
FIG. 1C is a conceptual view of an inspection measurement sub-system, in accordance with another embodiment of the present disclosure.

FIG. 1C is a conceptual view illustrating an inspection measurement sub-system 102, in accordance with another embodiment of the present disclosure. In one embodiment, the illumination pathway 116 and the collection pathway 128 contain separate elements. For example, the illumination pathway 116 may utilize a first focusing element 134 to focus the illumination beam 114 onto the sample 104 and the collection pathway 128 may utilize a second focusing element 136 to collect radiation from the sample 104. In this regard, the numerical apertures of the first focusing element 134 and the second focusing element 136 may be different. Further, it is noted herein that the inspection measurement sub-system 102 depicted in FIG. 1C may facilitate multi-angle illumination of the sample 104, and/or more than one illumination source 112 (e.g. coupled to one or more additional detectors 126). In this regard, the inspection measurement sub-system 102 depicted in FIG. 1C may perform multiple metrology measurements. In another embodiment, one or more optical components may be mounted to a rotatable arm (not shown) pivoting around the sample 104 such that the angle of incidence of the illumination beam 114 on the sample 104 may be controlled by the position of the rotatable arm.

Figure 2:
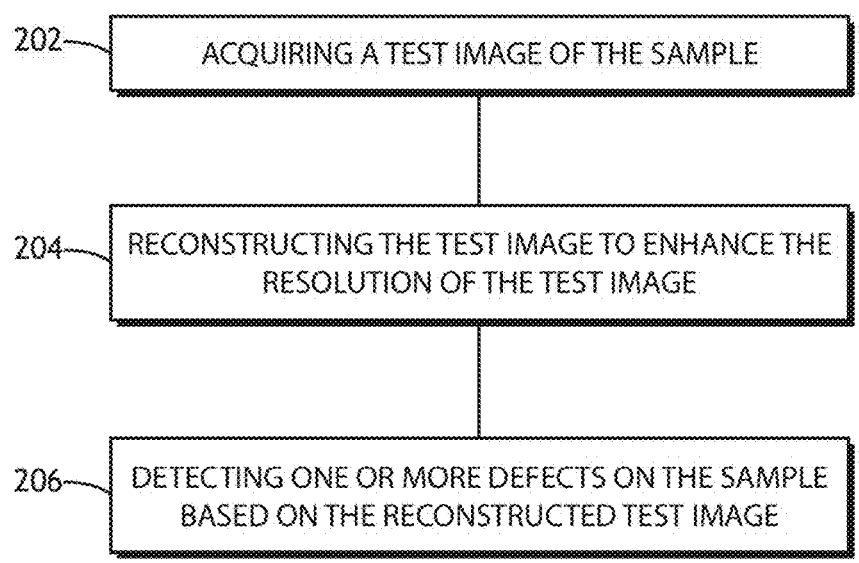
FIG. 2 is a flow diagram illustrating steps performed in a method for detecting defects in a sample, in accordance with one or more embodiments of the present disclosure.

FIG. 2 is a flow diagram illustrating steps performed in a method 200 for detecting defects in a sample, in accordance with one or more embodiments of the present disclosure. Applicant notes that the embodiments and enabling technologies described previously herein in the context of system 100 should be interpreted to extend to method 200. It is further noted, however, that the method 200 is not limited to the architecture of system 100.

Each of the steps of the method 200 may be performed as described further herein. The steps may be performed by one or more controllers (e.g. controller 106, or the like), which may be configured according to any of the embodiments described herein. In addition, the method described above may be performed by any of the system embodiments described herein. The method 200 may also include one or more additional steps that may be performed by controller or any system embodiments described herein.

In one embodiment, method 200 includes a step 202 of acquiring a test image. The test image may be an image (e.g. of sample 104) to be inspected for defects. Further, the test image may be formed by any method known in the art. For example, the test image may be, but is not required to be, generated at least in part using the inspection measurement sub-system 102. Accordingly, the test image may correspond to an optical image, a scanning electron microscope image, a particle-beam image, or the like. By way of another example, the test image may be stored by the inspection system 100. For example, the test image may be stored within the memory device 110 of controller 106. In this regard, the inspection system 100 may operate as a virtual inspection system. By way of another example, the test image may be retrieved from an external source (e.g. a data storage system, a server, an additional inspection system, or the like).

In another embodiment, method 200 includes a step 204 of reconstructing the test image to enhance the resolution of the test image. Step 204 may include reconstructing the test image using any method or combination of methods known in the art to enhance the detection of defects. In another embodiment, method 200 includes a step 206 of detecting one or more defects on the sample based on the reconstructed test image. For example, step 206 may include detecting defects based on the reconstructed test image using any technique known in the art. For example, portions of the reconstructed test image may be analyzed and compared to repeated portions of the test image, a reference image, design data, or the like for the detection of defects within the test image.

In one embodiment, step 204 includes reconstructing the test image by image interpolation. Step 204 may include reconstructing the test image using any interpolation technique known in the art such as, but not limited to, bilinear interpolation, cubic interpolation, Lanczos interpolation, nearest neighbor interpolation, B-spline interpolation, or sinc interpolation. For example, step 204 may include interpolating the test image to increase the resolution of the test image (e.g. upscale the image) beyond the resolution provided by the inspection system. For example, step 204 may include interpolating the test image to modify the pixel size and/or spacing to dimensions at or below dimensions of features on the sample. In this regard, location information associated with detected defects may be correlated to relevant sample features.

In another embodiment, step 204 includes reconstructing the image by deconvolution.

Figure 3:
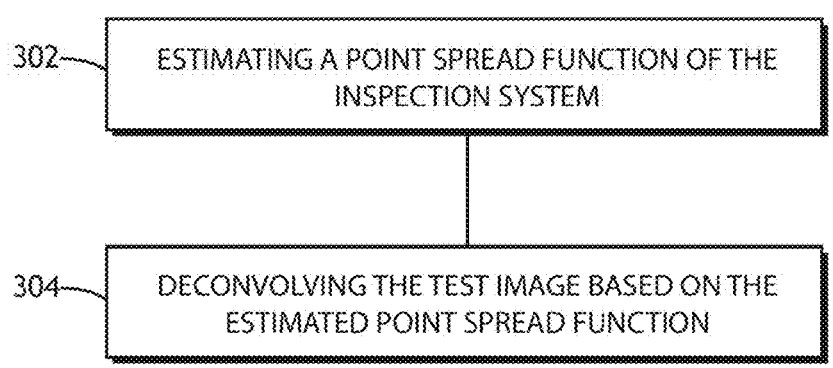
FIG. 3 is a flow diagram illustrating sub-steps of a defect detection method, in accordance with one or more embodiments of the present disclosure.

FIG. 3 is a flow diagram illustrating steps performed in step 204 of method 200, in accordance with one or more embodiments of the present disclosure. In one embodiment, step 204 includes a step 302 of estimating the PSF of the inspection system (e.g. inspection measurement sub-system 102, or the like). In another embodiment, step 204 includes a step 304 of deconvolving the test image based on the estimated PSF.

Imaging systems such as inspection systems typically provide an image that is a distorted representation of a sample. Sources of the distortion may include, but are not limited to, diffraction by components of the imaging system, aberrations of components of the imaging system, interference effects, motion of the sample, motion of the imaging system, or turbulence. In a general sense, the systematic distortions by the imaging system may be described by a point spread function (PSF). The PSF may be characterized as an image of a point source by the imaging system, which is typically a blur pattern. In this regard, an image provided by an imaging system may be modeled as a convolution of the true distribution (e.g. an ideal image) and the PSF. For example, an image $I(x,y)$ may be modeled as:

$$I(x,y) \approx O(x,y) * p(x,y), \tag{1}$$

where $O(x,y)$ is the ideal image and $p(x,y)$ is the PSF.

The image $I(x,y)$ may further be modeled to include assumptions of the distribution of noise, n. For example, the image $I(x,y)$ may be modeled as:

$$I(x,y) \approx O(x,y) * h(x,y) + n \tag{2}$$

for a Gaussian noise distribution. By way of another example, the image $I(x,y)$ may be modeled as:

$$I(x,y) \approx n(O(x,y) * h(x,y)) \tag{3}$$

for Poisson or impulse noise distributions.

As described previously herein, it is typically prohibitively difficult to define the exact PSF associated with the generation of a particular image by an imaging system due to the nature of the sources of distortion. Further, the PSF may vary as a function of both the spatial location of an object point in the field of view of the imaging system as well as the depth of the object. Accordingly, step 302 may include generating an estimate of the PSF of the inspection system that approximates the expected distortions of the inspection system.

Additionally, in the context of defect inspection in which features on the sample being imaged are smaller than the resolution of the inspection system, the PSF may be a function of the local design pattern. In this regard, it may be impractical to define a global PSF suitable for deconvolving an arbitrary image of a sample. Accordingly, it may be impractical to fully reconstructing an image of the sample to closely resemble the actual pattern of features on the sample. However, it may be the case that fully reconstructing an image to closely resemble the actual pattern of features on the sample may not be necessary for the purposes of defect detection. Rather, a realistic objective of deconvolution may be to increase the signal to noise ratio of the defect signals. For example, deconvolution may facilitate the contrast between defect signals and non-defect signals in an image. In this regard, an estimation of a global PSF in step 302 may provide an acceptable and practical reconstructed image.

In another embodiment, a global PSF is estimated based on a Fourier transform of a combination (e.g. a linear combination) of apertures of the inspection system. For example, step 302 may include generating an estimate of the PSF based on a Fourier transform of a linear combination of the illumination aperture (e.g. corresponding to a spatial distribution of illumination provided by the illumination source 112) and the collection aperture of the illumination system.

Figure 4C:
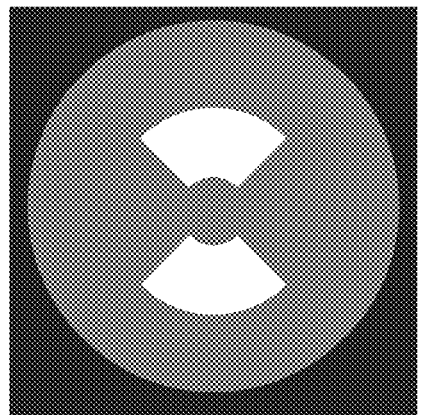
FIG. 4C is a plot of a linear combination of the illumination aperture and the collection aperture, in accordance with one or more embodiments of the present disclosure.
Figure 4B:
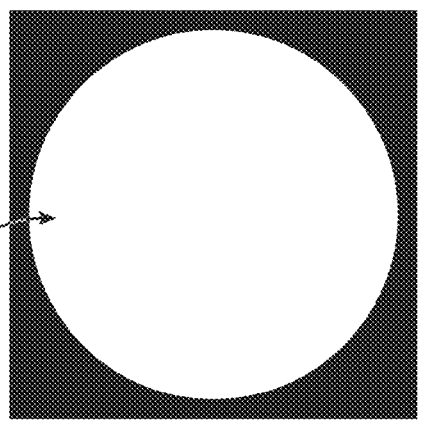
FIG. 4B is a plot of a collection aperture of an inspection system, in accordance with one or more embodiments of the present disclosure.
Figure 4A:
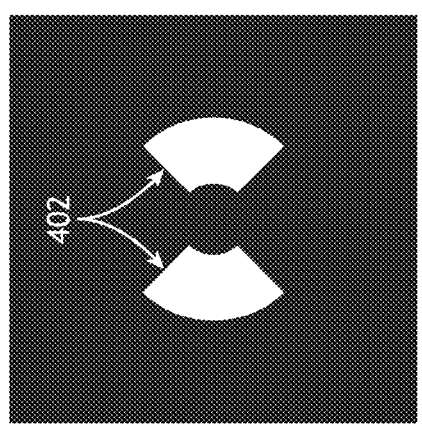
FIG. 4A is a plot of an illumination aperture of an inspection system, in accordance with one or more embodiments of the present disclosure.

FIGS. 4A through 4E illustrate the estimation of the PSF of an inspection system based on a linear combination of an illumination aperture and collection aperture. FIG. 4A is a plot 400 of an illumination aperture of an inspection system, in accordance with one or more embodiments of the present disclosure. For example, the illumination source 112 may have an illumination profile corresponding to plot 400. In one embodiment, the illumination aperture includes two illumination poles 402. In one instance, the two illumination poles 402, when projected onto a sample 104, may provide off-axis illumination. FIG. 4B is a plot 404 of a collection aperture of an inspection system, in accordance with one or more embodiments of the present disclosure. For example, the objective lens 124 of the inspection measurement sub-system 102 may have a circular collection aperture 406 corresponding to plot 404 that corresponds to 0.9 NA (e.g. of the objective lens 124). It is noted herein that the illumination and collection apertures may correspond to pupil planes of the inspection system. In this regard, a particular spatial position in the illumination or collection apertures may correspond to illumination entering or exiting the system at a particular angle. Accordingly, plots 400 and 404 may depict the relative strength of light propagating through the inspection system according to the entrance or exit angle.

FIG. 4C is a plot 408 of a linear combination of the illumination aperture of plot 400 and the collection aperture of plot 404, in accordance with one or more embodiments of the present disclosure. For example, plot 408 may illustrate the sum of the illumination aperture of plot 400 weighted by 0.8 and the collection aperture of plot 404 weighted by 0.2. It is to be understood, however, that the exemplary patterns within the illumination and collection apertures as well as the values of the weighting factors associated with FIGS. 4A through 4C are provided solely for illustrative purposes and should not be interpreted as limiting. In a general sense, the illumination and collection apertures may have any pattern. Further, the illumination and collection apertures may include grayscale values corresponding to a transmissivity of the aperture. Additionally, the linear combination of the illumination and collection apertures may be weighted with any combination of weights distributing the relative contributions. It is noted herein that weighting the illumination aperture heavily relative to the collection aperture may provide an estimation of the distribution of angles of illumination passing through the pupils of the inspection system. In another embodiment, weighting parameters may be generated from a customized function based on parameters of the inspection system (e.g. the inspection measurement sub-system 102, or the like) such as, but not limited to, the numeric aperture (NA) or the illumination angle.

Figure 4E:
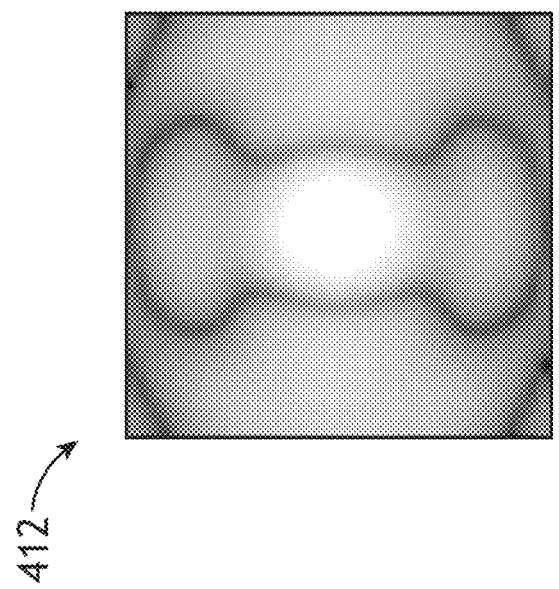
FIG. 4E is a plot of the estimated PSF of the inspection system in a logarithmic scale based on a 2D Fourier transform of the linear combination of the illumination and collection apertures illustrated in FIG. 4C, in accordance with one or more embodiments of the present disclosure.
Figure 4D:
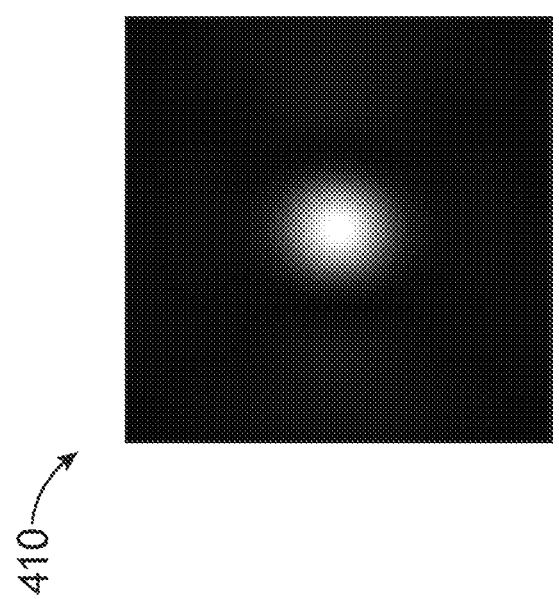
FIG. 4D is a plot of an estimated PSF of the inspection system in a linear scale based on a 2D Fourier transform of the linear combination of the illumination and collection apertures illustrated in FIG. 4C, in accordance with one or more embodiments of the present disclosure.

FIG. 4D is a plot 410 of an estimated PSF of the inspection system in a linear scale based on a 2D Fourier transform of the linear combination of the illumination and collection apertures illustrated in FIG. 4C, in accordance with one or more embodiments of the present disclosure. FIG. 4E is a plot 412 of the estimated PSF of the inspection system in a logarithmic scale based on a 2D Fourier transform of the linear combination of the illumination and collection apertures illustrated in FIG. 4C, in accordance with one or more embodiments of the present disclosure. For example, the PSF illustrated in FIGS. 4D and 4E may represent an estimation of the response of the inspection system to a point source.

Deconvolution (e.g. as performed in step 304, or the like) is typically an ill-posed inverse problem in that a unique solution may not exist. A reconstructed version of the image produced by an imaging system, O'(x,y), may be determined by any deconvolution technique known in the art suitable for enhancing the detection of defects in an image of a sample (e.g. a test image).

In some embodiments, one or more processing steps may be performed in the Fourier domain (e.g. using spatial Fourier transforms of an image to be reconstructed). In one embodiment, equation (1) may be represented as:

$$v = H\xi, \qquad (4)$$

where $\xi$ is the Fourier transform of the ideal image (O), $v$ is the Fourier transform of the observed image (I), and H is the Fourier transform of the PSF (e.g. the optical transfer function (OTF)).

In one embodiment, a reconstructed image, $\xi'$, is generated by directly inverting the OTF:

$$\xi' = H^{-1} v. \qquad (5)$$

Further, a small constant, c, may be added to equation (5) to avoid singularities. For example, a reconstructed image, $\xi'$, may be generated according to:

$$\xi' = (H^{-1} + c) v. \qquad (5)$$

In another embodiment, the inverse matrix, $H^{-1}$, may be determined based on the known or expected frequency-dependent signal to noise ratio (SNR(f)):

$$\frac{H^*}{H^* H + c \cdot SNR(f)^{-2}}, \qquad (6)$$

where H* represents the complex conjugate of H. In this regard, the inverse matrix, $H^{-1}$ may represent a Wiener filter that filters spatial frequencies based on the signal to noise ratio. For example, high spatial frequencies of images may typically have relatively larger signal to noise ratios and may thus be more strongly filtered by the Wiener filter.

In another embodiment, an image may be reconstructed based on a maximum likelihood calculation. For example, an image that minimizes the least square error may be characterized as:

$$\xi' = \mathrm{argmin}_\xi \|v - H\xi\|^2. \quad (7)$$

In another embodiment, one or more regularization factors may be included in a minimization to enforce prior knowledge, constrain the solution, and/or avoid amplifying noise. For example, regularization factors may constrain the image based on smoothness, sparseness, a gradient, or the like. In one instance, an image that minimizes the least square error constrained by regularization may be characterized as:

$$\xi' = \mathrm{argmin}_\xi [\|v - H\xi\|^2 + \lambda \rho(\xi)], \quad (8)$$

where $\lambda$ is a regularization parameter and $\rho(\xi)$ is a constraining function.

In another embodiment, a reconstructed image may be generated using an iterative technique that converges to a maximum likelihood solution. For example, step 204 may include, but is not limited to, reconstructing an image using a Richardson-Lucy deconvolution technique. For example, a Richardson-Lucy deconvolution may provide an iterative solution converging to a maximum likelihood image (e.g. reconstructed image O') based on an assumption of a Poisson noise distribution. In this regard, a likelihood probability of an observed image I given an ideal image O and a PSF h may be characterized as:

$$p(I \mid O, h) = \prod_{x \in D} \frac{[(O * h)(x)]^{I(x)}}{I(x)!} \exp\{-(O * h)(x)\}, \quad (9)$$

where D represents the spatial coordinates of the images I and O. Further, the likelihood probability of equation (9) is maximized by minimizing the negative log likelihood, E (e.g. a cost function):

$$E_{I,h}[O] = -\log p(I \mid O, h) \approx \int \left[\left(O * h - I - I \cdot \log \frac{O * h}{I}\right)(x)\right] dx. \quad (10)$$

A maximum likelihood estimation may then be characterized as:

$$O^* = \arg\min_O -\log p(I \mid O, h) \quad (11)$$

and an iterative solution for the reconstructed image may be found as:

$$O^{k+1} = \left(h^* * \frac{I}{h * O^k}\right) \odot O^k, \quad (12)$$

where k is an integer representing the iteration number, $O^k$ is the kth iteration of the reconstructed image.

Figure 5A:
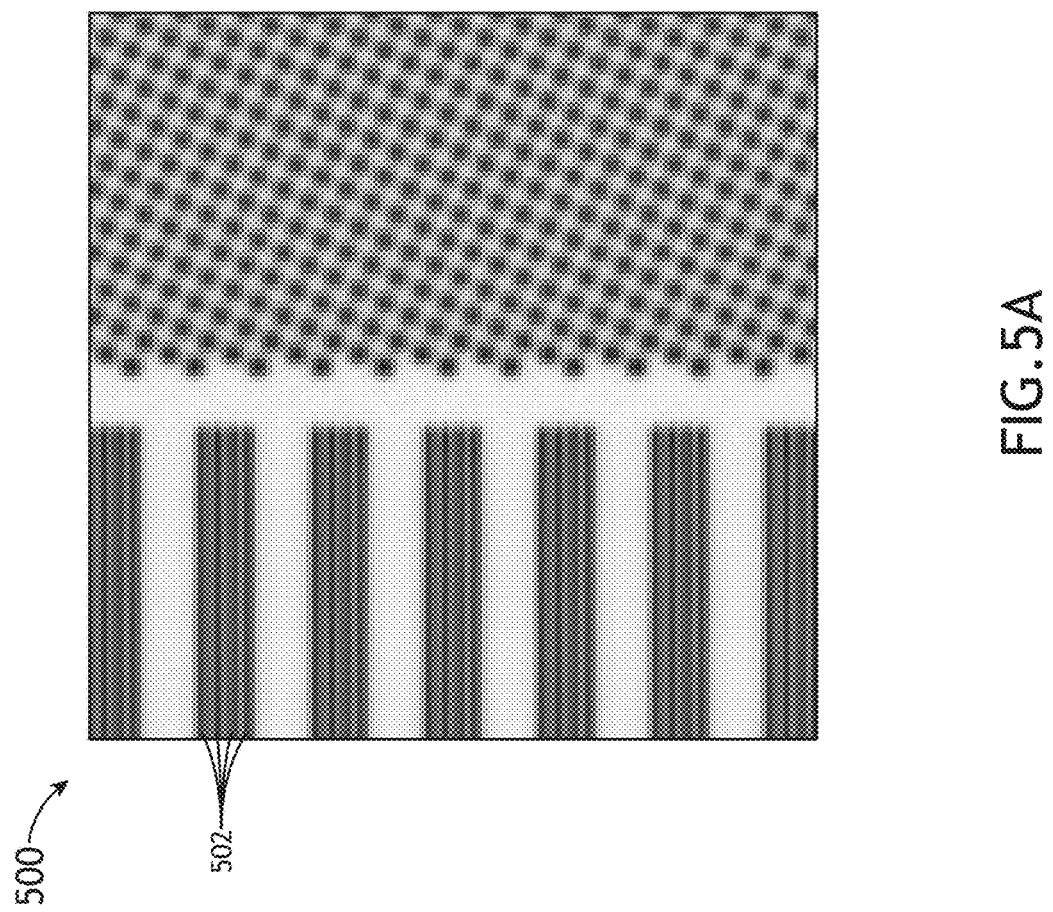
FIG. 5A is an observed image of a sample, in accordance with one or more embodiments of the present disclosure.
Figure 5B:
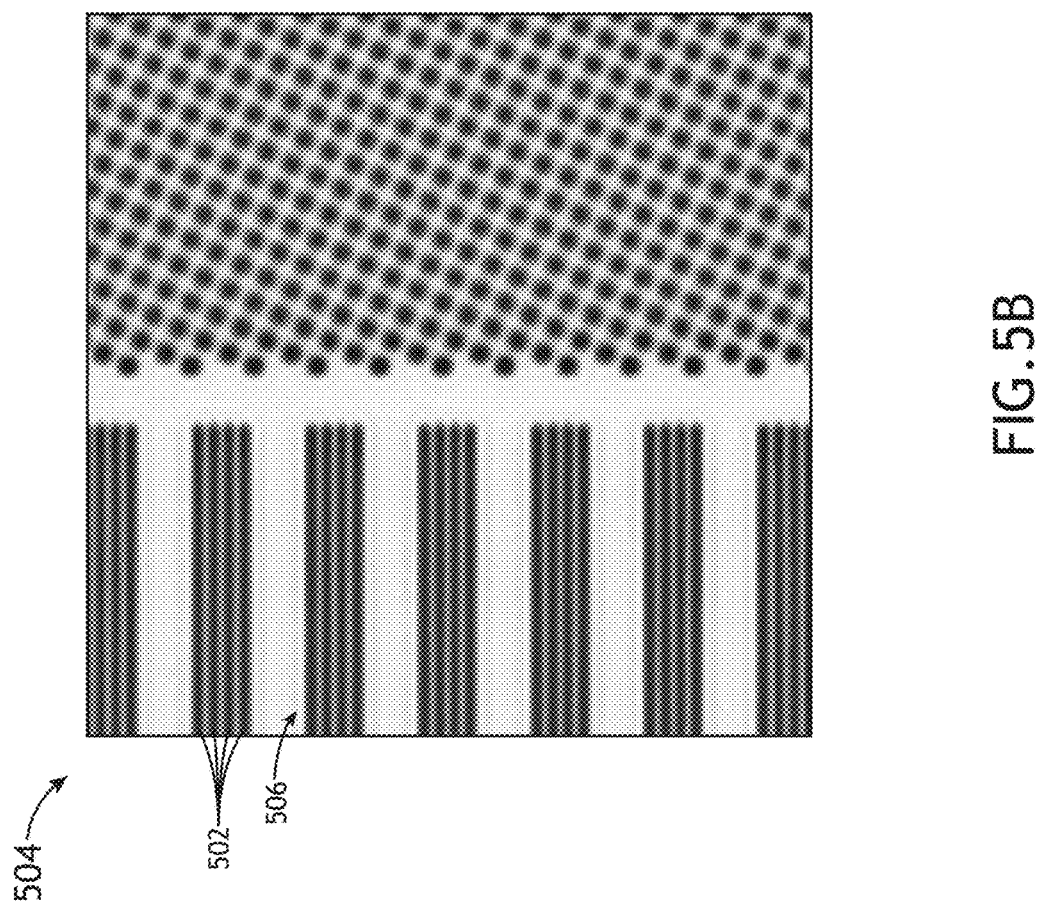
FIG. 5B is a reconstructed image corresponding to a reconstructed version of the observed image generated by 10 iterations of Richardson-Lucy convolution, in accordance with one or more embodiments of the present disclosure.
Figure 5C:
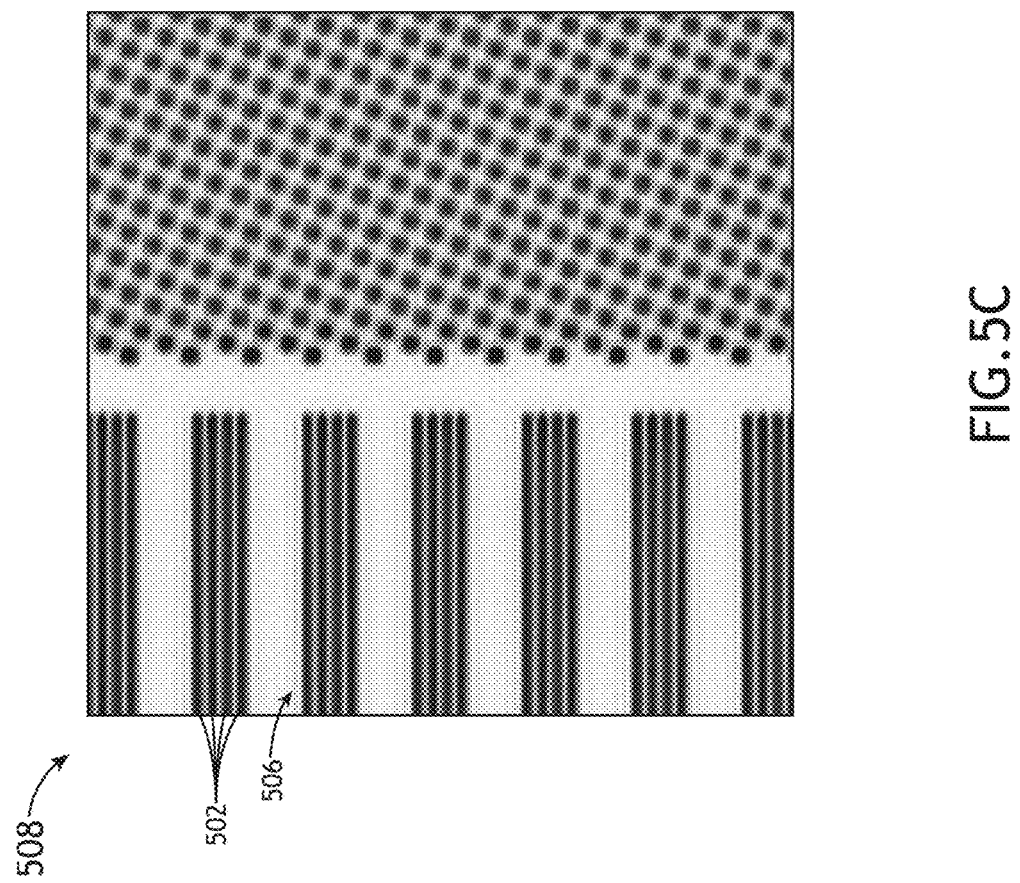
FIG. 5C is a reconstructed image corresponding to a reconstructed version of the observed image generated by 100 iterations of Richardson-Lucy convolution, in accordance with one or more embodiments of the present disclosure.

FIGS. 5A through 5C illustrate an application of Richardson-Lucy deconvolution on an image. FIG. 5A is an observed image 500 of a sample (e.g. acquired by an inspection system), in accordance with one or more embodiments of the present disclosure. The image includes a series of linear features 502 that are not clearly resolved. FIG. 5B is a reconstructed image 504 corresponding to a reconstructed version of the observed image 500 generated by 10 iterations of Richardson-Lucy convolution, in accordance with one or more embodiments of the present disclosure. The reconstructed image 504 exhibits enhanced resolution. For example, the edges of the linear features 502 are sharper than in the observed image 500, though they are not clearly defined. Further, the positions of the linear features 502 are unchanged with respect to FIG. 5A. In this regard, the reconstructed image 504 may provide superior performance when utilized for the detection of defects. For example, the location of identified defects may be more precisely determined and correlated to features on the sample using the reconstructed image 504 relative to the observed image 500. However, Richardson-Lucy deconvolution may generate artifacts in the image that may negatively impact the detection of defects. For example, ringing artifacts 506 (e.g. associated with an amplitude oscillation near an edge, or the like) are not present in the observed image 500 and are further not representative of the sample. Accordingly, the presence of the ringing artifacts 506 may negatively impact defect detection performance. FIG. 5C is a reconstructed image 508 corresponding to a reconstructed version of the observed image 500 generated by 100 iterations of Richardson-Lucy convolution, in accordance with one or more embodiments of the present disclosure. In the reconstructed image 508, the edges of the linear features are sharper than the reconstructed image 504 obtained using 10 iterations. However, the ringing artifacts 506 are amplified as well. In some applications, artifacts introduced by the deconvolution process (e.g. the ringing artifacts 506, and the like) may offset advantages in defect detection obtained by deconvolution.

In another embodiment, step 304 includes reconstructing an observed image using a regularized deconvolution technique in which one or more regularization parameters constrain the resulting images. In this regard, artifacts associated with the deconvolution process may be mitigated. A regularization parameter utilized in step 304 may be of any type of regularization parameter known in the art. For example, a regularization parameter may constrain one or more aspects of the image according to prior knowledge (e.g. known or estimated constraints associated with the ideal image). For example, image constraint regularization parameters may include, but are not limited to, constraints on the gradients or the smoothness within the image.

In another embodiment, step 304 includes a maximum a posterior (MAP analysis. For example, a reconstructed image may be characterized as $O' = \arg\max_O p(O/I,h) = \arg\max_O p(I/O,h)p(I)$ where $p(O/I,h) = p(I/O,h)p(O)/p(I)$ represents the posterior probability according to Bayes' Rule.

In another embodiment, step 304 includes reconstructing an image using regularized Richardson-Lucy (RRL) deconvolution. For example, a cost function, E, associated with a regularized Richardson-Lucy deconvolution may be characterized as:

$$E_{I,h}^{RRL}[O] = \int \left[\left(O * h - I - I \cdot \log \frac{O * h}{I}\right)(x) + \alpha \cdot \Psi(O)\right] dx, \quad (13)$$

where $\alpha$ is a regularization factor and $\Psi(O)$ is a regularization function evaluated for the ideal image, O. The corresponding iterative solution for the regularized Richardson-Lucy deconvolution may be expressed as:

$$O^{k+1} = \left( \frac{h^* * \frac{I}{h*O^k}}{1 - \alpha \cdot div(\Psi(O))} \right) \odot O^k. \quad (14)$$

In one instance, a regularization factor includes a Total Variation factor, which may be expressed as:

$$\Psi(O) = |\nabla O|. \quad (15)$$

In another instance, a regularization factor includes a Tikhonov-Miller factor, which may be expressed as:

$$\Psi(O) = |\nabla O|^2. \quad (16)$$

In another instance, a regularization factor includes a Bilateral factor, which may be expressed as:

$$\Psi(O) = \int_x \int_{x' \in D} \exp\left\{ -\frac{|x-x'|^2}{2\sigma_s} \right\} \left( 1 - \exp\left\{ -\frac{|O(x) - O(x')|^2}{2\sigma_r} \right\} \right) dx dx'. \quad (17)$$

It is to be understood that the examples of regularization factors described herein are provided solely for illustrative purposes and should not be interpreted as limiting. A deconvolution performed may include any type of regularization factor known in the art including, but not limited to maximum a posterior deconvolution.

FIGS. 5D through 5F illustrate applications of regularized Richardson-Lucy deconvolution on an image. FIG. 5D is a reconstructed image 510 generated using regularized Richardson-Lucy deconvolution with a Total Variation regularization factor, in accordance with one or more embodiments of the present disclosure. FIG. 5E is a reconstructed image 512 generated using regularized Richardson-Lucy deconvolution with a Tikhonov-Miller regularization factor, in accordance with one or more embodiments of the present disclosure. FIG. 5F is a reconstructed image 514 generated using regularized Richardson-Lucy deconvolution with a bilateral regularization factor, in accordance with one or more embodiments of the present disclosure. It is noted herein that the different regularization parameters provide enhanced resolution relative to the observed image (e.g. FIG. 5A), though the different regularization parameters may provide different tradeoffs. For example, different regularization parameters may provide different tradeoffs between the sharpness of the edges of the linear features 502 and the strength of artifacts such as ringing artifacts 506, the strength of artifacts associated with weaker signals, computation time, or the like. In this regard, a regularization parameter may be selected (e.g. by the controller 106 of the inspection system 100, or the like) to facilitate the detection of defects based on specific performance metrics and/or a particular feature pattern on a sample. For example, performance characteristics of defect detection such as, but not limited to defect salience, defect position (e.g. in relation to sample features), or the determination of care areas in an inspection recipe may be improved through reconstruction of images from an inspection system (e.g. test images and/or reference images).

It may be the case that reconstruction of one or more images provided by an inspection system may not fully recover some spatial frequencies associated with the feature pattern on the sample that were not captured by the inspection system in the first place. However, reconstruction may facilitate defect detection by increasing the signal to noise ratio and/or the contrast associated with defects in an image.

FIGS. 6A through 6C illustrate a comparison between image reconstruction based on cubic image interpolation and regularized Richardson-Lucy deconvolution. FIG. 6A is an image 602 of a sample reconstructed using cubic interpolation, in accordance with one or more embodiments of the present disclosure. FIG. 6B is an image 604 of the same portion of the sample reconstructed using regularized Richardson-Lucy deconvolution, in accordance with one or more embodiments of the present disclosure. FIG. 6C is a plot 606 illustrating the gray level associated with a slice of both image 602 of FIG. 6A and image 604 of FIG. 6B, in accordance with one or more embodiments of the present disclosure. In plot 606, the relative positions of features remain constant for both reconstruction methods. In this regard, the positions of defects observed in reconstructed images may be precisely determined. Further, as seen in plot 606, image reconstruction using regularized Richardson-Lucy deconvolution may provide both increased contrast in the image (e.g. increased peak to valley signal strength associated with image features) and sharper definitions of the shape of image features (e.g. steeper slopes and/or narrower peaks associated with image features).

Figure 7:
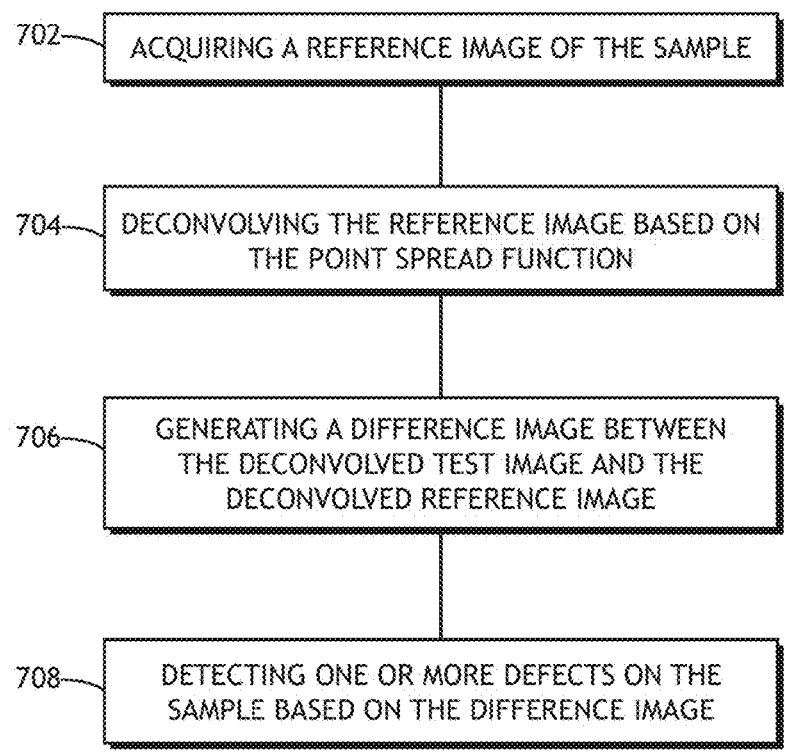
FIG. 7 is a flow diagram illustrating sub-steps of a method for the detection of defects based on a difference image generated using a reconstructed test image and a reconstructed reference image, in accordance with one or more embodiments of the present disclosure.

As previously described herein, an inspection system (e.g. inspection system 100, or the like) may detect defects on a sample by generating a difference image between a test image of the sample under inspection and a reference image (e.g. based on one or more images of additional dies or cells on the sample under inspection or a reference sample). FIG. 7 is a flow diagram illustrating steps performed in step 206 of method 200 for the detection of defects based on a difference image generated using a reconstructed test image and a reconstructed reference image, in accordance with one or more embodiments of the present disclosure. In one embodiment, step 206 includes a step 702 of acquiring a reference image of the sample. For example, the reference image may be, but is not required to be, generated at least in part using the inspection measurement sub-system 102. Accordingly, the reference image may correspond to an optical image, a scanning electron microscope image, a particle-beam image, or the like. Further, the reference image may be generated by a combination of images (e.g. of dies and/or cells having the same pattern of features) and/or design data. By way of another example, the reference image may be stored by the inspection system 100. For example, the reference image may be stored within the memory device 110 of controller 106. In this regard, the inspection system 100 may operate as a virtual inspection system. By way of another example, the reference image may be retrieved from an external source (e.g. a data storage system, a server, an additional inspection system, or the like).

In another embodiment, step 206 includes a step 704 of reconstructing the reference image based on the point spread function. For example, the reference image may be reconstructed using any technique such as, but not limited to, interpolation, deconvolution, or regularized deconvolution. In another embodiment, step 206 includes a step 706 of generating a difference image between the reconstructed test image and the reconstructed reference image. In another embodiment, step 206 includes a step 708 of detecting one or more defects on the sample based on the difference image. For example, defects may be attributed to differences between the reconstructed test image and the reconstructed reference image.

Figure 8:
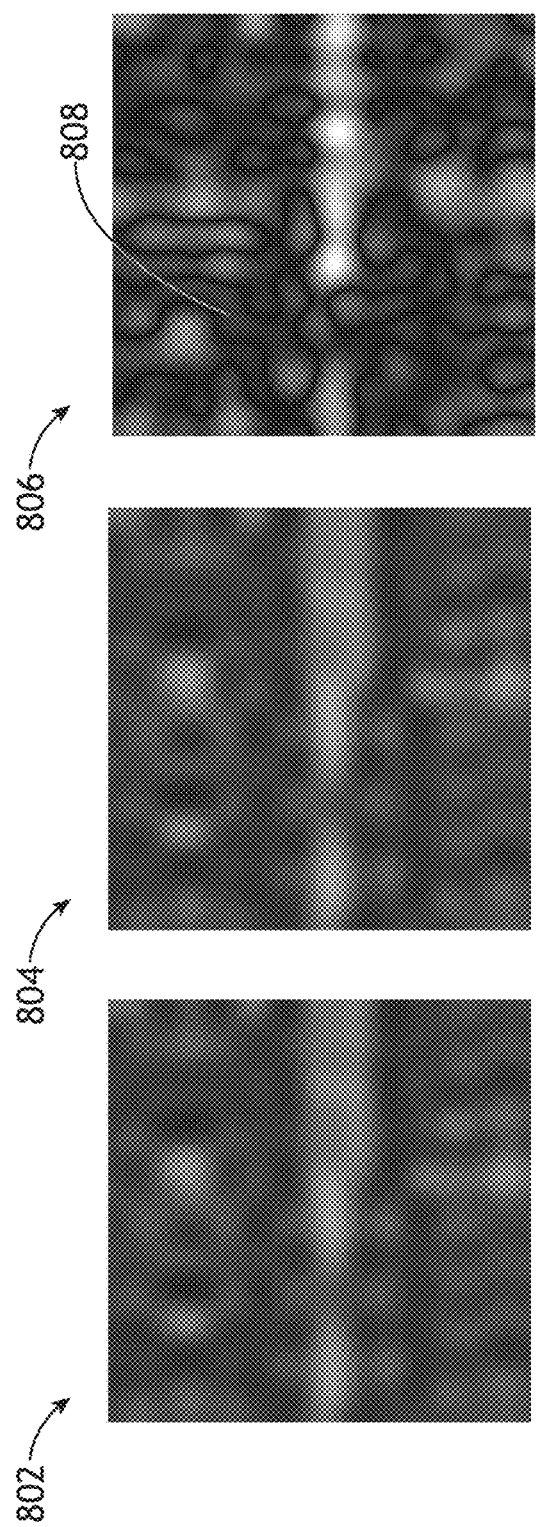
FIG. 8 includes a reconstructed test image, a reconstructed reference image, and a reconstructed difference image illustrating the generation of a difference signal based on a reconstructed test image and a reconstructed reference image, in accordance with one or more embodiments of the present disclosure.

FIG. 8 includes a reconstructed test image, a reconstructed reference image, and a reconstructed difference image illustrating the generation of a difference signal based on a reconstructed test image and a reconstructed reference image, in accordance with one or more embodiments of the present disclosure. Image 802 represents a reconstructed version of a reference image of a desired pattern of features generated using regularized Richardson-Lucy deconvolution. Image 804 represents a reconstructed version of a test image of the sample to be inspected for defects generated using regularized Richardson-Lucy deconvolution. It may be the case that certain aspects of the features of the sample are not fully resolved by the inspection system such that the images appear blurry, even after reconstruction. Image 806 represents a difference image based on a difference between image 802 and image 804 with a gain of 10×. Further, the difference image 806 has a signal to noise ratio of 14.2 and is suitable for the detection of defects. However, it may be the case that residual artifacts associated with the deconvolution may be present in the difference image and thus negatively impact the defect detection performance. For example, although regularization tends to mitigate the generation of artifacts in a reconstructed image (e.g. see FIGS. 5A through 5F), it may be the case that the reconstructed image contains some artifacts 808. Further, differences between the test image and the reference image due to the defects of interest may modify the distribution of artifacts in the test image relative to the reference image. Accordingly, the difference image (e.g. image 806) may contain visible artifacts 808 that may negatively impact defect detection based on the difference image.

In another embodiment, when defect detection is based on a difference image, the test image is reconstructed with an additional sparse-distribution regularization term. It is recognized herein that, in the context of defect detection, a test image and a reference image are intentionally similar, except for the potential presence of defects in the test image. Further, the defect signals in the test image are typically sparsely distributed in the spatial domain. Accordingly, incorporating a sparse-distribution regularization parameter into the reconstruction of the test image (but not the reference image) may enhance the defect signal and mitigate artifacts associated with the reconstruction process (e.g. see FIG. 8).

For example, a test image may be, but is not required to be, reconstructed using sparsity-inspired regularized Richardson-Lucy (SRRL) deconvolution based on a cost function including a sparse distribution regularization term:

$$E_{I,h}^{SRRL}[O] = \int \left[ \left( O*h - I - I \log\frac{O*h}{I} \right)(x) + (\alpha \cdot \Psi(O)) + (\beta \cdot |O - \overline{O}|^P) \right] dx, \quad (18)$$

where β is a sparse distribution regularization factor and 0<p≤1.

Figure 9:
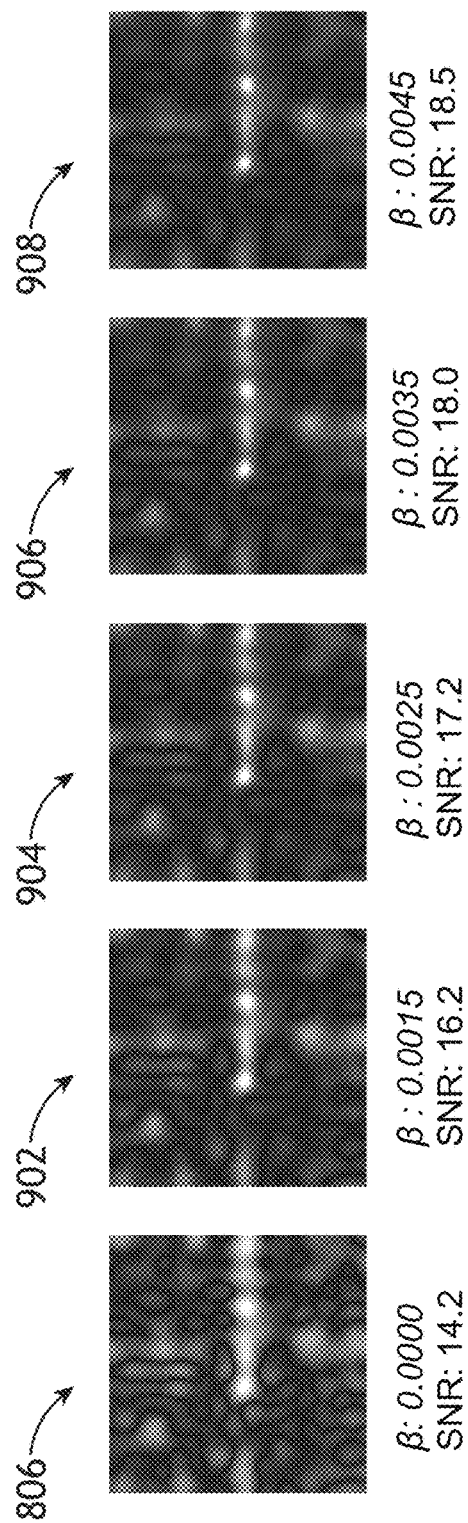
FIG. 9 includes difference images generated using a reconstructed reference image and a reconstructed test image based on different values of a sparse-distribution regularization parameter, in accordance with one or more embodiments of the present disclosure.

FIG. 9 includes difference images generated using a reconstructed reference image and a reconstructed test image based on different values of a sparse-distribution regularization parameter, in accordance with one or more embodiments of the present disclosure. For example, images 902-908 are generated with values of β (e.g. of equation (18)) ranging from 0.0015 to 0.0045, Ψ(O)=|∇O|, and exhibit signal to noise ratios increasing from 16.2 to 18.5. In this regard, as the sparse-distribution regularization parameter β is increased, residual artifacts associated with the regularized Richardson-Lucy deconvolution are increasingly suppressed without noticeable shape distortion in the image. Accordingly, defects in the signal may be more clearly detected.

In another embodiment, locations of defects detected based on a reconstructed test image (e.g. by method 200) with or without the generation of a difference image are correlated to features on the sample. For example, locations of defects detected based on a reconstructed test image may be correlated to design data. In this regard, defect detection based on image reconstruction may facilitate the localization of defects to sub-pixel accuracy (e.g. based on an area of the sample associated with a single pixel of an observed test image obtained by the inspection system).

Figure 10:
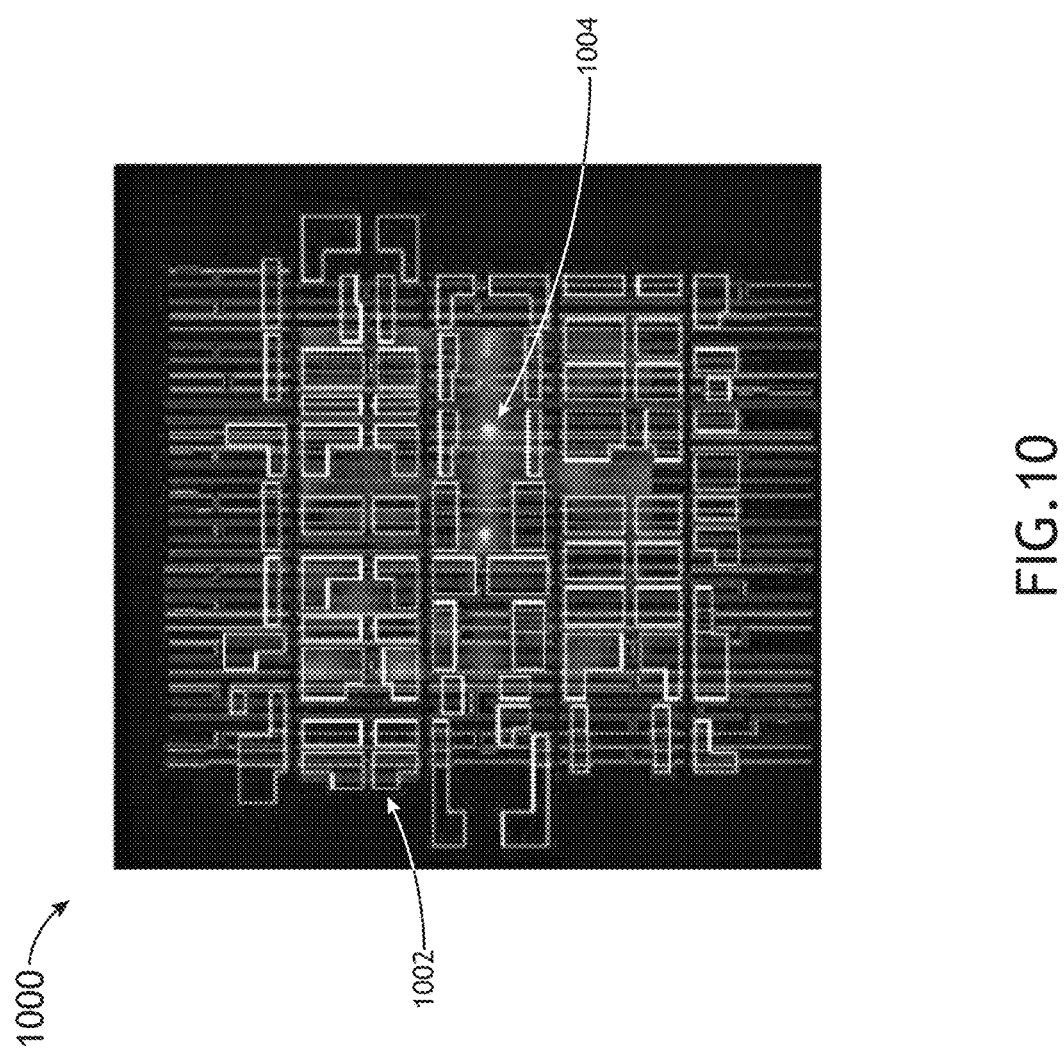
FIG. 10 is an image illustrating a map of sample features based on design data overlaid with defects detected based on a difference image generated using a reconstructed reference image and a reconstructed test image with a sparse-distribution regularization parameter, in accordance with one or more embodiments of the present disclosure.

FIG. 10 is an image 1000 illustrating a map of sample features 1002 based on design data overlaid with defects 1004 detected based on a difference image generated using a reconstructed reference image and a reconstructed test image with a sparse-distribution regularization parameter, in accordance with one or more embodiments of the present disclosure. In one embodiment, defect signals 1004 are precisely located within the context of features 1002 that are smaller than the resolution of the inspection system utilized to generate the test and/or reference images.

The term "design data" as used in the present disclosure generally refers to the physical design of an integrated circuit and data derived from the physical design through complex simulation or simple geometric and Boolean operations. In addition, an image of a reticle acquired by a reticle inspection system and/or derivatives thereof may be used as a proxy or proxies for the design data. Such a reticle image or a derivative thereof may serve as a substitute for the design layout in any embodiments described herein that uses design data. Design data and design data proxies are described in U.S. Pat. No. 7,676,077 by Kulkarni issued on Mar. 9, 2010; U.S. patent application Ser. No. 13/115,957 by Kulkarni filed on May 25, 2011; U.S. Pat. No. 8,041,103 by Kulkarni issued on Oct. 18, 2011; and U.S. Pat. No. 7,570,796 by Zafar et al. issued on Aug. 4, 2009, all of which are incorporated herein by reference. Further, the use of design data in directing inspection processes is described generally in U.S. patent application Ser. No. 13/399,805 to Park, filed on Feb. 17, 2012, which is incorporated herein by reference in the entirety.

Design data may include characteristics of individual components and/or layers on the sample 104 (e.g. an insulator, a conductor, a semiconductor, a well, a substrate, or the like), a connectivity relationship between layers on the sample 104, or a physical layout of components and connections (e.g. wires) on the sample 104. In this regard, design data may include a plurality of design pattern elements corresponding to printed pattern elements on the sample 104.

It is noted herein that design data may include what is known as a "floorplan," which contains placement information for pattern elements on the sample 104. It is further noted herein that this information may be extracted from the physical design of a chip usually stored in GDSII or OASIS file formats. The structural behavior or process-design interactions may be a function of the context (surroundings) of a pattern element. By using the floor plan, the analysis proposed can identify pattern elements within the design data, such as polygons describing features to be constructed on a semiconductor layer. Further, the proposed method may provide the coordination information of these repeating blocks as well as contextual data (e.g. the positions of adjacent structures, or the like).

In one embodiment, design data includes one or more graphical representations (e.g. visual representations, symbolic representations, diagrammatic representations, or the like) of pattern elements. For example, design data may include a graphical representation of the physical layout of components (e.g. descriptions of one or more polygons corresponding to printed pattern elements fabricated on the sample 104). Further, design data may include a graphical representation of one or more layers of a sample design (e.g. one or more layers of printed pattern elements fabricated on the sample 104) or the connectivity between the one or more layers. As another example, design data may include a graphical representation of electrical connectivity of components on the sample 104. In this regard, the design data may include a graphical representation of one or more circuits or sub-circuits associated with the sample. In another embodiment, design data includes one or more image files containing graphical representations of one or more portions of the sample 104.

In another embodiment, design data includes one or more textual descriptions (e.g. one or more lists, one or more tables, one or more databases, or the like) of the connectivity of pattern elements of the sample 104. For example, design data may include, but is not limited to, netlist data, circuit simulation data, or hardware description language data. Netlists may include any type of netlist known in the art for providing a description of the connectivity of an electrical circuit including, but not limited to physical netlists, logical netlists, instance-based netlists, or net-based netlists. Further, a netlist may include one or more sub-netlists (e.g. in a hierarchal configuration) to describe circuits and/or sub-circuits on a sample 104. For example, netlist data associated with a netlist may include, but is not limited to, a list of nodes (e.g. nets, wires between components of a circuit, or the like), a list of ports (e.g. terminals, pins, connectors, or the like), a description of electrical components between the nets, (e.g. resistor, capacitor, inductor, transistor, diode, power source, or the like), values associated with the electrical components (e.g. a resistance value in ohms of a resistor, a voltage value in volts of a power source, frequency characteristics of a voltage source, initial conditions of components, or the like). In another embodiment, design data may include one or more netlists associated with specific steps of a semiconductor process flow. For example, a sample 104 may be inspected (e.g. by inspection system 100) at one or more intermediate points in a semiconductor process flow. Accordingly, design data utilized to generate care areas may be specific to the layout of the sample 104 at a current point in the semiconductor process flow. In this regard, a netlist associated with a particular intermediate point in a semiconductor process flow may be derived (e.g. extracted, or the like) from either the physical design layout in combination with a technology file (layer connectivity, electrical properties of each of the layers, and the like) or a netlist associated with a final layout of a sample 104 to include only components present on the wafer at the particular intermediate point in the semiconductor process flow.

In another embodiment, image reconstruction is applied to one or more patch images generated by the inspection system. For example, patch images may be generated to facilitate the classification of defects detected by the inspection system.

Figure 11:
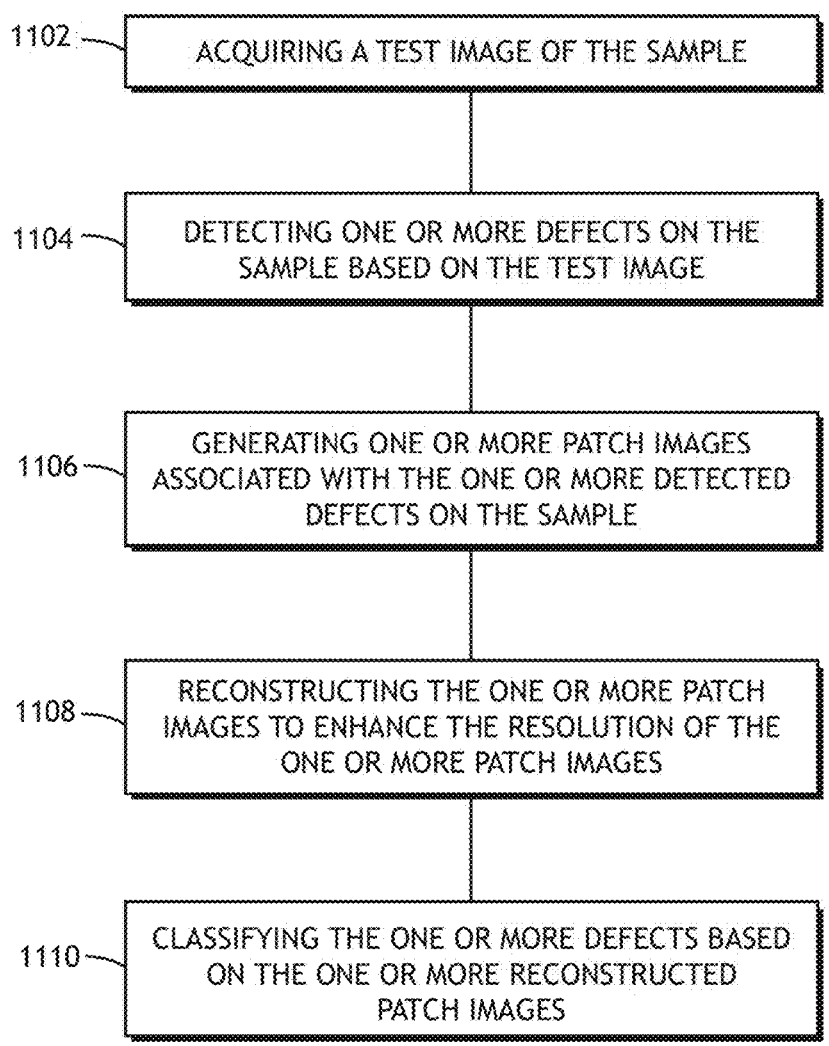
FIG. 11 is a flow diagram illustrating steps performed in a method for classifying defects in a sample based on reconstructed patch images, in accordance with one or more embodiments of the present disclosure.

FIG. 11 is a flow diagram illustrating steps performed in a method 1100 for classifying defects in a sample based on reconstructed patch images, in accordance with one or more embodiments of the present disclosure. Applicant notes that the embodiments and enabling technologies described previously herein in the context of system 100 should be interpreted to extend to method 1100. It is further noted, however, that the method 1100 is not limited to the architecture of system 100.

Each of the steps of the method 1100 may be performed as described further herein. The steps may be performed by one or more controllers (e.g. controller 106, or the like), which may be configured according to any of the embodiments described herein. In addition, the method described above may be performed by any of the system embodiments described herein. The method 1100 may also include one or more additional steps that may be performed by controller or any system embodiments described herein.

In one embodiment, method 1100 includes a step 1102 of acquiring a test image of the sample. In another embodiment, method 1100 includes a step 1104 of detecting one or more defects on the sample based on the test image. For example, step 1104 may include detecting one or more defects on the sample based on a reference image (e.g. based on a difference image associated with the test image and the reference image, or the like). By way of another example, step 1104 may include detecting one or more defects on the sample based on design data.

In another embodiment, method 1100 includes a step 1106 of generating one or more patch images associated with the one or more detected defects on the sample. For example, a patch image may include a portion of the test image surrounding a defect detected in step 1104. A patch image may be any size suitable for depicting a defect and relevant features of the test image.

In another embodiment, method 1100 includes a step 1108 of reconstructing the one or more patch images to enhance the resolution of the one or more patch images. For example, the one or more patch images may be reconstructed using any technique known in the art such as, but not limited to, interpolation or deconvolution. In one instance, the one or more patch images are reconstructed using regularized deconvolution (e.g. regularized Richardson-Lucy deconvolution, or the like).

In another embodiment, method 1100 includes a step 1110 of classifying the one or more defects based on the one or more reconstructed patch images. For example, defects may be classified according to any classification scheme known in the art based on the reconstructed patch images. In one instance, defects are classified based on the type of defect (e.g. electrical short to ground, bridge defect, or the like). In another instance, defects are classified based on the sample feature proximate to the defect. In another embodiment, defects may be binned according to the classification to generate a pareto of defects.

In another embodiment, image reconstruction is applied to multiple test images. For example, an inspection system may generate multiple test images of the sample using multiple modes of illumination. It is recognized herein that the spatial resolution of an imaging system depends on the angles of illumination captured from the sample (e.g. the diffracted orders of illumination associated with various spatial frequency content of the object). Further, the diffracted orders of illumination collected by the collection aperture may depend on the angle at which light illuminates the sample. Illumination at normal incidence may tend to result in the collection of relatively few diffraction orders and thus provides an image having relatively low spatial resolution. In contrast, illumination at large angles may tend to result in the collection of relatively more diffraction orders and thus provides an image having relatively high spatial resolution.

In the case that multiple angles of illumination are simultaneously directed at the sample (e.g. through a fixed illumination aperture), the collection optics effectively combine the various diffracted orders associated with the multiple angles of illumination to generate the image. In another embodiment of the present disclosure, an inspection system generates multiple test images with varying modes of illumination (e.g. varying incident angles of illumination directed towards the sample). Each test image may be reconstructed to enhance the resolution of the test images. Further, the reconstructed test images may be combined to a single combined image for defect detection. In another embodiment, defects may be detected at least in part based on the individual reconstructed test images.

Figure 12:
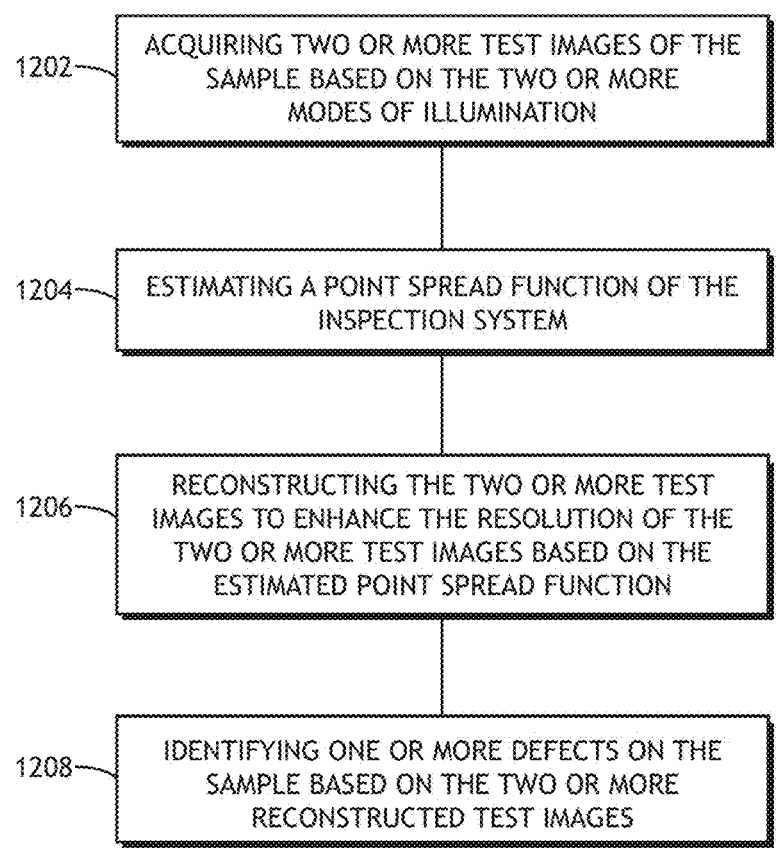
FIG. 12 is a flow diagram illustrating steps performed in a method for detecting defects in a sample, in accordance with one or more embodiments of the present disclosure.

FIG. 12 is a flow diagram illustrating steps performed in a method 1200 for detecting defects in a sample, in accordance with one or more embodiments of the present disclosure. Applicant notes that the embodiments and enabling technologies described previously herein in the context of system 100 should be interpreted to extend to method 1200. It is further noted, however, that the method 1200 is not limited to the architecture of system 100.

Figure 13:
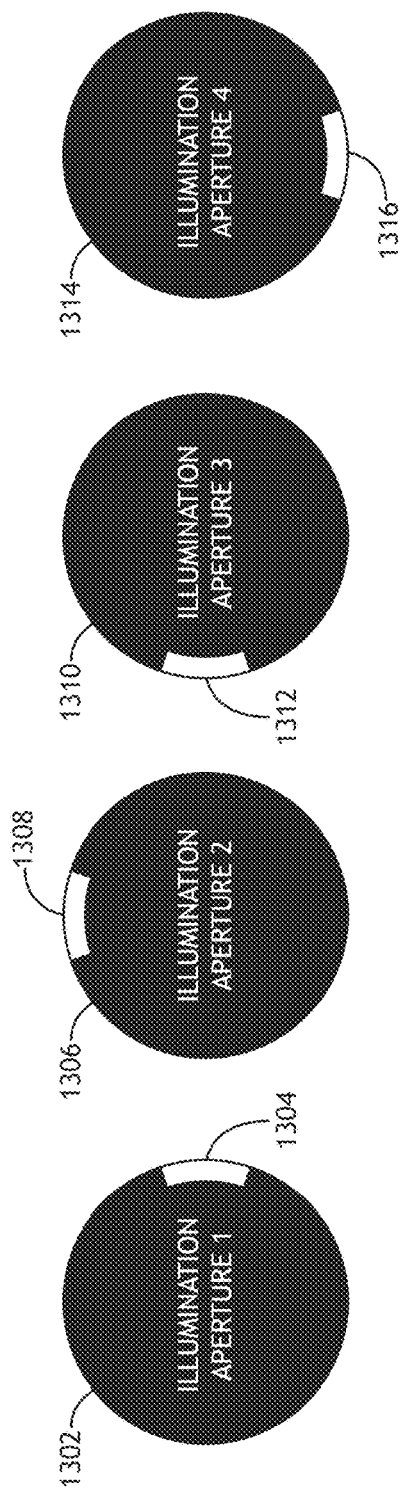
FIG. 13 is a conceptual view of four edge-contrast illumination modes oriented to illuminate the sample from different directions, in accordance with one or more embodiments of the present disclosure.

In one embodiment, the method includes a step 1202 of acquiring two or more test images of the sample based on the two or more modes of illumination. The modes of illumination associated with step 1202 may have any distribution known in the art suitable for tailoring the angular distribution of illumination on the sample. FIG. 13 is a conceptual view of four edge-contrast illumination modes oriented to illuminate the sample from different directions, in accordance with one or more embodiments of the present disclosure. In one embodiment, a first illumination aperture 1302 includes a first illumination mode 1304. In another embodiment, a second illumination aperture 1306 includes a second illumination mode 1308. In another embodiment, a third illumination aperture 1310 includes a third illumination mode 1312. In another embodiment, a fourth illumination aperture 1314 includes a fourth illumination mode 1316. For example, an inspection system (e.g. inspection measurement sub-system 102, or the like) may sequentially illuminate the sample with each of the four illumination apertures 1302, 1306, 1310, 1314 and generate a test image associated with each.

In another embodiment, the method 1200 includes a step 1204 of estimating a PSF of the inspection system. For example, step 1204 may include estimating a separate PSF for each test image based on the corresponding illumination aperture used to generate the test image.

In another embodiment, the method 1200 includes a step 1206 of reconstructing the two or more test images to enhance the resolution of the two or more test images based on the estimated point spread function. For example, the step 1206 may include reconstructing each of the test images using the estimated PSFs generated in step 1204. The test images may be reconstructed using any method such as, but not limited to, interpolation or deconvolution. In one instance, the test images may be reconstructed using regularized deconvolution (e.g. regularized Richardson-Lucy deconvolution, or the like).

In another embodiment, the method 1200 includes a step 1208 of identifying one or more defects on the sample based on the two or more reconstructed test images. For example, step 1208 may include generating a combined image (e.g. a fused image) based on the reconstructed test images generated in step 1206 and detecting defects based on the combined image. The combined image may be generated by any method known in the art such as, but not limited to, additive combination or multiplicative combination. By way of another example, step 1208 may include detecting defects based at least in part on any of the individual reconstructed images.

In another embodiment, image reconstruction is used to recover portions of a defect signal impacted by anti-aliasing techniques. For example, a pixel size of an inspection system is typically selected, at least in part, based on throughput or light budget considerations. For example, relatively larger pixel sizes may provide increased throughput and require less illumination intensity (e.g. a lower light level) from the illumination source (e.g. illumination source 112, or the like) than relatively smaller pixel sizes. However, larger pixel sizes may suffer from aliasing noise. An inspection system may utilize an anti-aliasing technique to mitigate any aliasing noise. For example, an inspection system may intentionally introduce blur into generated images that mitigates the aliasing noise. In one instance, an inspection system may introduce blur through the use of an anti-aliasing filter. In another instance, an inspection system may introduce blur directly during the image acquisition process. An anti-aliasing method in TDI-based imaging is described generally in U.S. Pat. No. 8,947,521, issued on Feb. 3, 2015, which is incorporated herein by reference in its entirety.

In another embodiment, image reconstruction is utilized to improve defect detectability in images generated using anti-aliased images. In this regard, image reconstruction may enhance the resolution of an anti-aliased image to recover a portion of the spatial frequencies impacted by the anti-aliasing technique.

Figure 14:
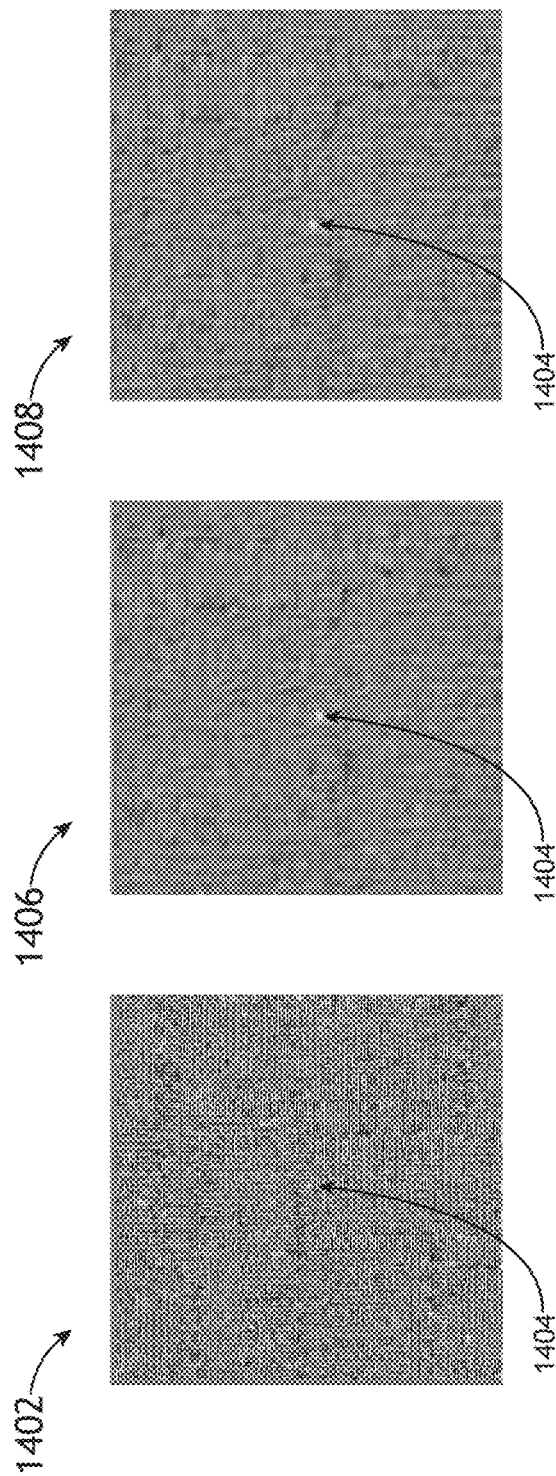
FIG. 14 includes images illustrating the enhancement of defect detectability in anti-aliased images, in accordance with one or more embodiments of the present disclosure.

FIG. 14 includes images illustrating the enhancement of defect detectability in anti-aliased images, in accordance with one or more embodiments of the present disclosure. For example, image 1402 includes a difference image that suffers from aliasing noise (e.g. an aliased difference image). A defect 1404 is visible in image 1402, but has a low contrast due to a signal to noise ratio of 1.2. Image 1406 includes an anti-aliased difference image. The anti-aliased difference image has a signal to noise ratio of 2.0, making the defect 1404 more clearly detectable than for the aliased difference image. Image 1408 includes a reconstructed difference image having a signal to noise ratio of 2.4, making the defect 1404 more clearly detectable than in images 1402, 1406. Image 1408 of FIG. 14 is reconstructed using Lanczos interpolation. However, it is to be understood that any reconstruction technique may be utilized to enhance the defect detectability of anti-aliased images such as, but not limited to regularized deconvolution. In one embodiment, the reconstructed difference image is generated by reconstructing a reference image with regularized deconvolution to minimize artifacts and by reconstructing an aliased test image using regularized deconvolution with an additional sparse-distribution regularization parameter.

In another embodiment, image reconstruction is utilized to configure a detection recipe of an inspection system. For example, a run-time parameter, such as, but not limited to, the light level of the illumination source (e.g. illumination source 112, or the like) may be determined by acquiring a configuration image of a sample, reconstructing the configuration image (e.g. to enhance the contrast of the configuration image to be suitable for defect detection), measuring the dynamic range, and adjusting the light level based on the measured dynamic range. By way of another example, the definition of care areas (e.g. localized portions of the sample to be inspected) may be enhanced through image reconstruction. For example, a configuration image of the sample may be generated and then reconstructed by the inspection system. In this regard, care areas may be defined with a high degree of accuracy and precision (e.g. sub-pixel precision as illustrated in FIG. 10, or the like).

In another embodiment, image reconstruction may facilitate the set-up and/or training of recipes associated with design-based detection algorithms such as, but not limited to pixel-to-design analysis (PDA), context-based imaging (CBI), or template-based imaging (TBI).

Referring again to FIG. 1, the inspection system 100 may include any inspection sub-system known in the art.

The one or more processors 108 of a controller 106 may include any processing element known in the art. In this sense, the one or more processors 108 may include any microprocessor-type device configured to execute algorithms and/or instructions. In one embodiment, the one or more processors 108 may consist of a desktop computer, mainframe computer system, workstation, image computer, parallel processor, or any other computer system (e.g., networked computer) configured to execute a program configured to operate the inspection system 100, as described throughout the present disclosure. It is further recognized that the term "processor" may be broadly defined to encompass any device having one or more processing elements, which execute program instructions from a non-transitory memory device 110. Further, the steps described throughout the present disclosure may be carried out by a single controller 106 or, alternatively, multiple controllers. Additionally, the controller 106 may include one or more controllers housed in a common housing or within multiple housings. In this way, any controller or combination of controllers may be separately packaged as a module suitable for integration into inspection system 100. Further, the controller 106 may analyze data received from the detector 126 and feed the data to additional components within the memory device 110 or external to the inspection system 100.

The memory device 110 may include any storage medium known in the art suitable for storing program instructions executable by the associated one or more processors 108. For example, the memory device 110 may include a non-transitory memory medium. By way of another example, the memory device 110 may include, but is not limited to, a read-only memory, a random access memory, a magnetic or optical memory device (e.g., disk), a magnetic tape, a solid state drive and the like. It is further noted that memory device 110 may be housed in a common controller housing with the one or more processors 108. In one embodiment, the memory device 110 may be located remotely with respect to the physical location of the one or more processors 108 and controller 106. For instance, the one or more processors 108 of controller 106 may access a remote memory (e.g., server), accessible through a network (e.g., internet, intranet and the like). Therefore, the above description should not be interpreted as a limitation on the present invention but merely an illustration.

In another embodiment, the inspection system 100 may include a display (not shown). In another embodiment, the display is communicatively coupled to the controller 106. For example, the display may be communicatively coupled to one or more processors 108 of controller 106. In this regard, the one or more processors 108 may display one or more of the various results of the present invention on display.

The display device may include any display device known in the art. In one embodiment, the display device may include, but is not limited to, a liquid crystal display (LCD). In another embodiment, the display device may include, but is not limited to, an organic light-emitting diode (OLED) based display. In another embodiment, the display device may include, but is not limited to a CRT display. Those skilled in the art should recognize that a variety of display devices may be suitable for implementation in the present invention and the particular choice of display device may depend on a variety of factors, including, but not limited to, form factor, cost, and the like. In a general sense, any display device capable of integration with a user interface device (e.g., touchscreen, bezel mounted interface, keyboard, mouse, trackpad, and the like) is suitable for implementation in the present invention.

In another embodiment, the inspection system 100 may include a user interface device (not shown). In one embodiment, the user interface device is communicatively couple to the one or more processors 108 of controller 106. In another embodiment, the user interface device may be utilized by controller 106 to accept selections and/or instructions from a user. In some embodiments, described further herein, the display may be used to display data to a user. In turn, a user may input selection and/or instructions (e.g., a user selection of inspection regions) responsive to inspection data displayed to the user via display device.

The user interface device may include any user interface known in the art. For example, the user interface may include, but is not limited to, a keyboard, a keypad, a touchscreen, a lever, a knob, a scroll wheel, a track ball, a switch, a dial, a sliding bar, a scroll bar, a slide, a handle, a touch pad, a paddle, a steering wheel, a joystick, a bezel input device or the like. In the case of a touchscreen interface device, those skilled in the art should recognize that a large number of touchscreen interface devices may be suitable for implementation in the present invention. For instance, the display device may be integrated with a touchscreen interface, such as, but not limited to, a capacitive touchscreen, a resistive touchscreen, a surface acoustic based touchscreen, an infrared based touchscreen, or the like. In a general sense, any touchscreen interface capable of integration with the display portion of the display device 105 is suitable for implementation in the present invention. In another embodiment, the user interface may include, but is not limited to, a bezel mounted interface.

Further, the system 100 may be configured as a "real" or a "virtual" inspection system. For example, the system 100 may generate actual images or other output data associated with the sample 104. In this regard, the system 100 may be configured as an "real" inspection system, rather than a "virtual" system. By way of another example, a storage medium (not shown) and the controller 106 described herein may be configured as a "virtual" inspection system. Accordingly, the system 100 may not operate on a physical sample, but may rather reproduce and/or stream stored data (e.g. data stored in a memory medium 110, or the like) as if a physical sample were being scanned. In this regard, the output of a "detector" may be data that was previously generated by one or more detectors (e.g. a detector 126) of an actual inspection system in a previous step (e.g. all grayscale values associated with a voltage contrast image, or the like). Systems and methods configured as "virtual" inspection systems are described in commonly assigned U.S. Pat. No. 8,126,255 issued on Feb. 28, 2012, and U.S. Pat. No. 9,222,895, issued on Dec. 29, 2015, both of which are incorporated by reference in their entirety.

The determination of defect and fault sources are generally described in U.S. Pat. No. 6,920,596, issued on Jul. 19, 2005, U.S. Pat. No. 8,194,968, issued on Jun. 5, 2015, and U.S. Pat. No. 6,995,393, issued on Feb. 7, 2006, which are incorporated herein by reference in their entirety. Device property extraction and monitoring is generally described in U.S. Pat. No. 8,611,639, issued on Dec. 17, 2013. The use of dual-energy electron flooding for neutralization of a charged substrate is generally described in U.S. Pat. No. 6,930,309, issued on Aug. 16, 2005, which is incorporated herein by reference in its entirety. The use of reticles in inspection systems is generally described in U.S. Pat. No. 6,529,621, issued on Mar. 4, 2003, U.S. Pat. No. 6,748,103, issued on Jun. 8, 2004, and U.S. Pat. No. 6,966,047, issued on Nov. 15, 2005, which are incorporated herein by reference in their entirety. Generating an inspection process or inspection target is generally described in U.S. Pat. No. 6,691,052, issued on Feb. 10, 2004, U.S. Pat. No. 6,921,672, issued on Jul. 26, 2005, and U.S. Pat. No. 8,112,241, issued on Feb. 7, 2012, which are incorporated herein by reference in their entirety. Determination of critical areas of semiconductor design data is generally described in U.S. Pat. No. 6,948,141, issued on Sep. 20, 2005, which is incorporated by reference herein in its entirety.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:
1. An inspection system, comprising:
an illumination sub-system, comprising:
an illumination source configured to generate a beam of illumination; and
a set of illumination optics to direct the beam of illumination to a sample;
a collection sub-system, comprising:
a set of collection optics to collect illumination emanating from the sample; and
a detector configured to receive the collected illumination from the sample; and
a controller communicatively coupled to the detector, the controller including a memory device and one or more processors configured to execute program instructions configured to cause the one or more processors to:
acquire a test image of the sample;
estimating a point spread function of the inspection system as a transform of a combination of an illumination aperture and a collection aperture of the inspection system;
reconstruct the test image, based on the estimated point spread function, to enhance the resolution of the test image; and
detect one or more defects on the sample based on the reconstructed test image.

2. The inspection system of claim 1, wherein the estimating a point spread function of the inspection system as a transform of a combination of an illumination aperture and a collection aperture of the inspection system comprises:
estimating the point spread function of the inspection system as a Fourier transform of a linear combination of the illumination aperture and the collection aperture of the inspection system.

3. The inspection system of claim 1, wherein reconstructing the test image comprises:
deconvolving the test image based on the estimated point spread function.

4. The inspection system of claim 3, wherein deconvolving the test image comprises:
deconvolving the test image using at least one of direct inversion, a Wiener filter, maximum likelihood deconvolution, or maximum a posterior deconvolution.

5. The inspection system of claim 4, wherein deconvolving the test image using maximum likelihood deconvolution comprises:
deconvolving the test image using noise having at least one of a Gaussian or a Poisson distribution.

6. The inspection system of claim 5, wherein deconvolving the test image using maximum likelihood deconvolution comprises:
deconvolving the test image using Richardson-Lucy deconvolution based on the estimated point spread function.

7. The inspection system of claim 4, wherein deconvolving the test image using maximum a posterior deconvolution comprises:
deconvolving the test image using noise having at least one of a Gaussian or a Poisson distribution.

8. The inspection system of claim 3, wherein a cost function associated with deconvolving the test image includes a sparse distribution regularization parameter.

9. The inspection system of claim 8, wherein a cost function associated with deconvolving the test image further includes an image gradient regularization parameter.

10. The inspection system of claim 9, wherein the image gradient regularization parameter comprises:
at least one of a Total Variation regularization parameter, a Tikhonov-Miller regularization parameter, or a Bilateral regularization parameter.

11. The inspection system of claim 9, wherein detecting one or more defects on the sample based on the reconstructed test image comprises:
acquiring a reference image of the sample;
deconvolving the reference image based on the point spread function;
generating a difference image between the deconvolved test image and the deconvolved reference image; and
detecting one or more defects on the sample based on the difference image.

12. The inspection system of claim 11, wherein a cost function associated with deconvolving the reference image includes the image gradient distribution regularization parameter.

13. The inspection system of claim 1, wherein acquiring the test image of the sample includes acquiring the test image of the sample using an anti-aliasing technique, wherein the anti-aliasing technique suppresses aliasing noise in the test image, wherein reconstructing the test image to enhance the resolution of the test image recovers one or more spatial frequencies associated with the sample impacted by the anti-aliasing technique.

14. The inspection system of claim 13, wherein reconstructing the test image comprises:
interpolating the test image.

15. The inspection system of claim 14, wherein interpolating the test image comprises:
interpolating the test image using at least one of bilinear interpolation, cubic interpolation, Lanczos interpolation, nearest neighbor interpolation, B-spline interpolation, or sinc interpolation.

16. The inspection system of claim 13, wherein reconstructing the test image comprises:
estimating the point spread function of the inspection system; and
deconvolving the test image based on the estimated point spread function.

17. The inspection system of claim 1, wherein detecting one or more defects on the sample based on the reconstructed test image includes reporting one or more locations of the one or more defects on the sample.

18. An inspection system, comprising:
an illumination sub-system, comprising:
an illumination source configured to generate a beam of illumination; and
a set of illumination optics to direct the beam of illumination to a sample;
a collection sub-system, comprising:
a set of collection optics to collect illumination emanating from the sample; and
a detector configured to receive the collected illumination from the sample; and
a controller communicatively coupled to the detector, the controller including a memory device and one or more processors configured to execute program instructions configured to cause the one or more processors to:
acquire a test image of the sample;
detect one or more defects on the sample based on the test image;
generate one or more patch images associated with the one or more detected defects on the sample;
estimating a point spread function of the inspection system as a transform of a combination of an illumination aperture and a collection aperture of the inspection system;
reconstruct the one or more patch images, based on the estimated point spread function, to enhance the resolution of the one or more patch images; and
classify the one or more defects based on the one or more reconstructed patch images.

19. The inspection system of claim 18, wherein reconstructing the test image comprises:
deconvolving the one or more patch images based on the estimated point spread function.

20. A multi-mode inspection system, comprising:
an illumination sub-system, comprising:
an illumination source configured to generate two or more modes of illumination; and
a set of illumination optics to sequentially direct the two or more modes of illumination to a sample;
a collection sub-system, comprising:
a set of collection optics to collect illumination emanating from the sample, wherein the set of collection optics includes an adjustable collection aperture, wherein the adjustable collection aperture is configured to generate two or more collection modes, wherein the illumination sub-system includes two or more system modes formed from the two or more modes of illumination and the two or more collection modes; and
a detector configured to receive the collected illumination from the sample; and
a controller communicatively coupled to the detector, the controller including a memory device and one or more processors configured to execute program instructions configured to cause the one or more processors to:
acquire two or more test images of the sample based on the two or more system modes;
estimate a point spread function of the inspection system as a transform of a combination of an illumination aperture and a collection aperture of the inspection system;
reconstruct the two or more test images, based on the estimated point spread function, to enhance the resolution of the two or more test images based on the estimated point spread function; and
identify one or more defects on the sample based on the two or more reconstructed test images.

21. The multi-mode inspection system of claim 20, wherein estimating a point spread function of the inspection system comprises:
estimating the point spread function of the inspection system as a Fourier transform of a linear combination of an illumination aperture and a collection aperture of the inspection system.

22. The multi-mode inspection system of claim 20, wherein reconstructing the two or more test image comprises:
deconvolving the two or more test image based on the estimated point spread function.

23. The multi-mode inspection system of claim 22, wherein deconvolving the test image comprises:
deconvolving the two or more test images using Richardson-Lucy deconvolution based on the estimated point spread function.

24. The inspection system of claim 23, wherein a cost function associated with deconvolving the two or more test images includes a sparse distribution regularization parameter.

25. The multi-mode inspection system of claim 23, wherein a cost function associated with deconvolving the two or more test images further includes an image gradient regularization parameter.

26. The multi-mode inspection system of claim 25, wherein the image gradient regularization parameter comprises:
at least one of a Total Variation regularization parameter, a Tikhonov-Miller regularization parameter, or a Bilateral regularization parameter.

27. The multi-mode inspection system of claim 26, wherein detecting the one or more defects on the sample based on the two or more reconstructed test images comprises:
  combining the two or more reconstructed test images into a combined reconstructed test image; and
  detecting the one or more defects based on the combined reconstructed test image.

28. The multi-mode inspection system of claim 24, wherein identifying one or more defects on the sample based on the two or more reconstructed test images comprises:
  detecting one or more defects on the sample based on the two or more reconstructed test images.

29. The multi-mode inspection system of claim 28, wherein identifying one or more defects on the sample based on the two or more reconstructed test images further comprises:
  generating one or more patch images associated with the one or more detected defects on the sample; and
  classifying the one or more defects based on the one or more patch images.

30. An inspection system, comprising:
  an illumination sub-system, comprising:
  an illumination source configured to generate a beam of illumination; and
  a set of illumination optics to direct the beam of illumination to a sample;
  a collection sub-system, comprising:
  a set of collection optics to collect illumination emanating from the sample; and
  a detector configured to receive the collected illumination from the sample; and
  a controller communicatively coupled to the detector, the controller including a memory device and one or more processors configured to execute program instructions configured to cause the one or more processors to:
  configure a defect detection recipe, wherein configuring the defect detection recipe comprises:
    acquiring a configuration image of the sample;
    estimating a point spread function of the inspection system as a transform of a combination of an illumination aperture and a collection aperture of the inspection system; and
    reconstructing the configuration image of the sample, based on the estimated point spread function, to enhance the resolution of the configuration image; and
  detect one or more defects on the sample based on the defect detection recipe.

31. The inspection system of claim 30, wherein configuring the defect detection recipe further comprises:
  defining one or more care areas on the sample to be inspected based on the reconstructed configuration image.

32. The inspection system of claim 30, wherein configuring the defect detection recipe further comprises:
  measuring a dynamic range of the reconstructed configuration image; and
  adjusting a run-time parameter of the illumination source based on the measured dynamic range of the reconstructed configuration image.

33. The inspection system of claim 32, wherein the run-time parameter comprises:
  a light level of the illumination source.

34. The inspection system of claim 30, wherein configuring the defect detection recipe further comprises:
  training a design-based defect detection technique.

35. The inspection system of claim 34, wherein the design-based defect detection technique comprises:
  at least one of a pixel-to-design alignment technique, a context-based imaging technique, or a template based imaging technique.

* * * * *